Figure 2:
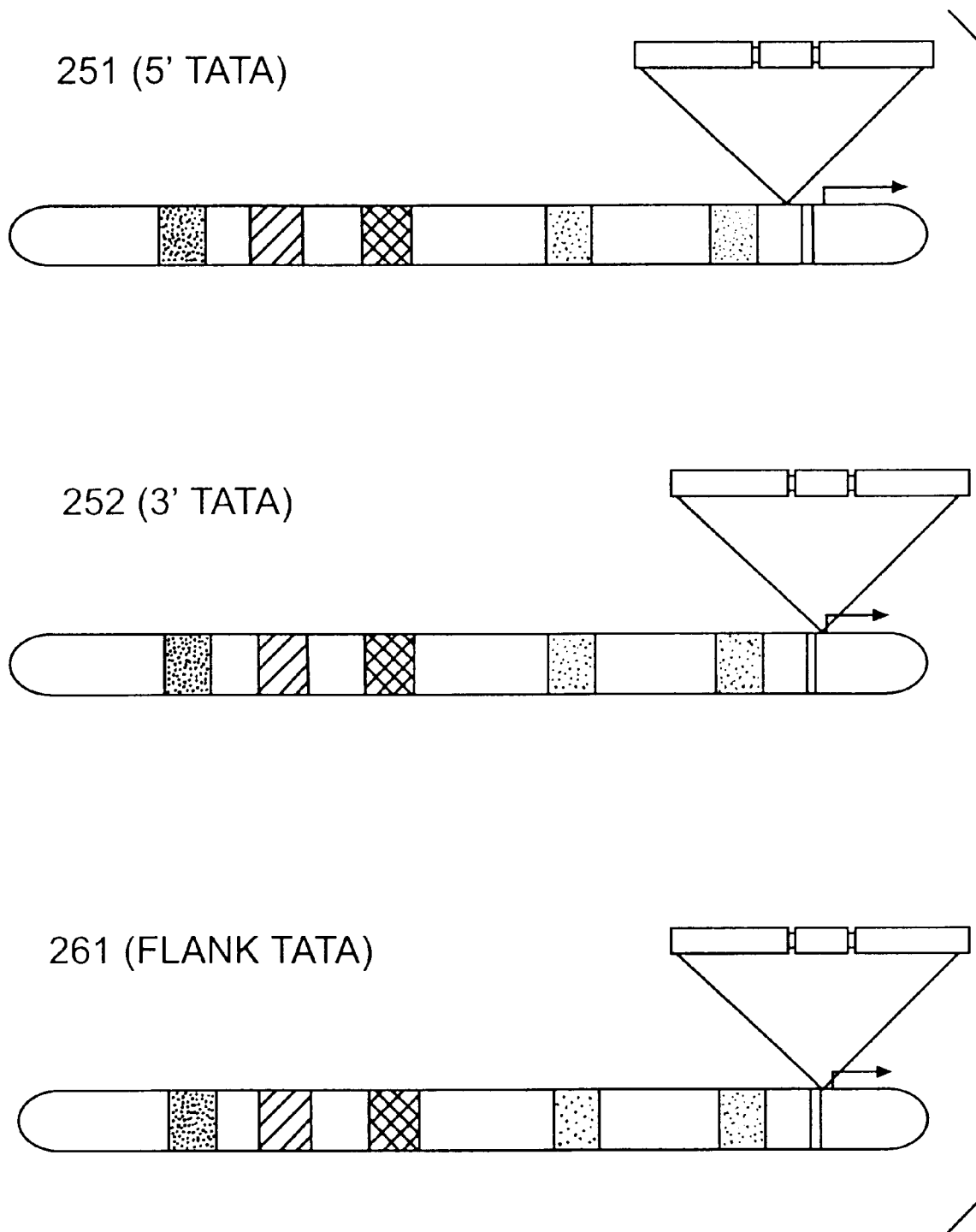

United States Patent [19]
Byrne

[11] Patent Number: 5,917,122
[45] Date of Patent: Jun. 29, 1999

[54] TETRACYCLINE REPRESSOR-MEDIATED BINARY REGULATION SYSTEM FOR CONTROL OF GENE EXPRESSION IN TRANSGENIC MICE

[76] Inventor: Guerard Byrne, 507 Madison Dr., East Windsor, N.J. 08520

[21] Appl. No.: 08/392,771

[22] PCT Filed: Aug. 26, 1993

[86] PCT No.: PCT/US93/08230
§ 371 Date: Feb. 24, 1995
§ 102(e) Date: Feb. 24, 1995

[87] PCT Pub. No.: WO94/04672
PCT Pub. Date: Mar. 3, 1994

Related U.S. Application Data

[63] Continuation-in-part of application No. 07/935,763, Aug. 26, 1992, abandoned.

[51] Int. Cl.$^6$ ............... C12N 5/00; C12N 15/00; C12N 15/09; C12N 15/63
[52] U.S. Cl. ............... 800/18; 435/6; 435/69.1; 435/70.1; 435/70.3; 435/91.4; 435/455; 435/462; 435/463; 435/325; 435/320.1; 536/24.1
[58] Field of Search ............... 800/2, 18; 435/6, 435/69.1, 70.1, 70.3, 91.4, 172.3, 240.2, 320.1, 455, 462, 463, 325; 935/6, 22, 24, 33, 34, 36; 536/24.1

[56] References Cited

U.S. PATENT DOCUMENTS

| | | | |
|---|---|---|---|
| 5,075,229 | 12/1991 | Hanson et al. | 435/172.3 |
| 5,221,778 | 6/1993 | Byrne et al. | 800/2 |

OTHER PUBLICATIONS

Byrne and Ruddle, 1989, "Multiplex gene regulation: A two–tiered aproach to transgene regulation in transgenic mice", Proc Natl Acad Sci 86:5473–5477.

Gatz et al., 1991, "Regulation of a modified CaMV 35S promoter by the Tn10–encoded Tet repressor in transgenic tobacco", Mol Gen Genet 227:229–237.

Gatz and Quail, 1988, "Tn10–encoded tet repressor can regulate an operator–containing plant promoter", Proc Natl Acad Sci 85:1394–1397.

Gatz et al., 1992, "Stringent repression and homogeneous de–repression bytetracycline of a modified CaMV 35S promoter in intact transgenic tobacco plants", Plant J 2(3):397–404.

Gossen and Bujard, 1992, "Tight control of gene expression in mammalian cells by tetracycline–responsive promoters", Proc Natl Acad Sci 89:5547–5551.

Khillan et al., 1988, "Gene transcativation mediated by the TAT gene of human immunodeficiency virus in transgenic mice", Nucl Acids Res 16(4):1423–1430.

Ornitz et al., 1991, "Binary system for regulatin transgene expression in mice: Targeting int–2 gene expression with yeast GAL4/UAS control elements", Proc Natl Acad Sci 88:698–702.

Wilde et al., 1992, "Control of gene expression in tobacco cells using a bacterial operator–repressor system", EMBO J 11(4):1251–1259.

P. Beufey et al. Embo J. 9(6) 1677–84, 1990.

J. Watson et al., Molecular Biol. of the Gene, 4$^{th}$ Ed., Benjamin/Cummings Publ. Co., Inc., (87), Menlo Park, CA, pp. 252–253 & 440–442.

T. Giordano et al., Gene, (90) 88(2): 288–8.

Primary Examiner—Jasemine C. Chambers
Assistant Examiner—Jill D. Martin
Attorney, Agent, or Firm—Larson & Taylor

[57] ABSTRACT

The present invention relates to a tetracycline repressor-mediated binary regulation system for the control of gene expression in transgenic mice. It is based, at least in part, on the discovery that, in a transgenic mouse that carries a first transgene under the control of a modified promoter comprising a tetR operator sequence and a second transgene encoding the tetR protein, expression of the first transgene may be efficiently induced by administering tetracycline to the mouse.

12 Claims, 23 Drawing Sheets

Tn 10

OPERATOR 1                    OPERATOR 2
TTGACACTCTATCATCATTGATAGAGTTATTTTACCACTCCCTATCAGTGATAGAG
(SEQ ID NO: 1)

OLIGONUCLEOTIDES
  EcoR1    OPERATOR 1           Hind3       OPERATOR 2                              Acc1
GAATTCGAT ACTCTATCATCATTGATAGAGT ATCAAGCTTA TCCGTATCAGTGATAGAGA TACCGTCGACCTC
(SEQ ID NO: 2)

ACTCTATCATCATTGATAGAGT TACTATTAAAA TCCCTATCAGTGATAGAGA
(SEQ ID NO: 3)

FIG. 1A

```
                             EcoR1        OP1                               linker
                        ggaattcgat-ACT CTA TCA TTG ATA GAG TAT CAA GCT TAT CCC OP2                    AccI
                        TAT CAG TGA TAG AGA-taccgtcgacctc (SEQ ID NO: 4)
```

*FIG. 1B*

```
         10           20           30           40
          *            *            *            *
ATG TCT AGA TTA GAT AAA AGT AAA GTG ATT AAC AGC GCA TTA GAG
 M   S   R   L   D   K   S   K   V   I   N   S   A   L   E>
___TETRACYCLINE REPRESSOR PROTEIN (TETR); CODON_START=1___>
___b___b___b___TETR REPRESSOR MRNA [SPLIT]_b___b___b___b___>
<___a_1520__a___a_903 TO 1526 OF TRN10TETR__a_1490__a___a___

50           60           70           80           90
       *            *            *            *            *
CTG CTT AAT GAG GTC GGA ATC GAA GGT TTA ACA ACC CGT AAA CTC
 L   L   N   E   V   G   I   E   G   L   T   T   R   K   L>
___TETRACYCLINE REPRESSOR PROTEIN (TETR); CODON START=1___>
___b___b___b___TETR REPRESSOR MRNA [SPLIT]_b___b___b___b___>
<1480_a___a___1470_903 TO 1526 OF TRN10TETR_0_a___a___1440a___

100          110          120          130
          *            *            *            *
GCC CAG AAG CTA GGT GTA GAG CAG CCT ACA TTG TAT TGG CAT GTA
 A   Q   K   L   G   V   E   Q   P   T   L   Y   W   H   V>
    TETRACYCLINE REPRESSOR PROTEIN (TETR); CODON START=1___>
___b___b___b___TETR REPRESSOR MRNA [SPLIT]_b___b___b___b___>
<___a_1430__a___a_903 TO 1526 OF TRN10TETR__a_1400__a___a___

140          150          160          170          180
          *            *            *            *            *
AAA AAT AAG CGG GCT TTG CTC GAC GCC TTA GCC ATT GAG ATG TTA
 K   N   K   R   A   L   L   D   A   L   A   I   E   M   L>
___TETRACYCLINE REPRESSOR PROTEIN (TETR); CODON_START=1___>
___b___b___b___TETR REPRESSOR MRNA [SPLIT]_b___b___b___b___>
<1390_a___a___1380_903 TO 1526 OF TRN10TETR_0_a___a___1350a___

190          200          210          220
          *            *            *            *
GAT AGG CAC CAT ACT CAC TTT TGC CCT TTA GAA GGG GAA AGC TGG
 D   R   H   H   T   H   F   C   P   L   E   G   E   S   W>
___TETRACYCLINE REPRESSOR PROTEIN (TETR); CODON_START=1___>
___b___b___b___TETR REPRESSOR MRNA [SPLIT]_b___b___b___b___>
<___a_1340__a___a_903 TO 1526 OF TRN10TETR__a_1310__a___a___
```

FIG. 5A

```
      230           240           250           260           270
       *             *             *             *             *
  CAA GAT TTT TTA CGT AAT AAC GCT AAA AGT TTT AGA TGT GCT TTA
    Q   D   F   L   R   N   N   A   K   S   F   R   C   A   L>
  ___TETRACYCLINE REPRESSOR PROTEIN (TETR); CODON_START=1____>
  __b___b___b___TETR REPRESSOR MRNA [SPLIT]_b___b___b___b___>
 <1300_a___a___1290_903 TO 1526 OF TRN10TETR_0_a___a___1260a___

280           290           300           310
             *             *             *             *

CTA AGT CAT CGC GAT GGA GCA AAA GTA CAT TTA GGT ACA CGG CCT
    L   S   H   R   D   G   A   K   V   H   L   G   T   R   P
  ___TETRACYCLINE REPRESSOR PROTEIN (TETR); CODON_START=1____>
  __b___b___b___TETR REPRESSOR MRNA [SPLIT]_b___b___b___b___>
 <___a_1250__a___a_903 TO 1526 OF TRN10TETR__a_1220__a___a___

320           330           340           350           360
       *             *             *             *             *

ACA GAA AAA CAG TAT GAA ACT CTC GAA AAT CAA TTA GCC TTT TTA
    T   E   K   Q   Y   E   T   L   E   N   Q   L   A   F   L>
  ___TETRACYCLINE REPRESSOR PROTEIN (TETR); CODON_START=1____>
  __b___b___b___TETR REPRESSOR MRNA [SPLIT]_b___b___b___b___>
 <1210_a___a___1200_903 TO 1526 OF TRN10TETR_0_a___a___1170a___

370           380           390           400
             *             *             *             *

TGC CAA CAA GGT TTT TCA CTA GAG AAT GCA TTA TAT GCA CTC AGC
    C   Q   Q   G   F   S   L   E   N   A   L   Y   A   L   S>
  ___TETRACYCLINE REPRESSOR PROTEIN (TETR); CODON START=1____>
  __b___b___b___TETR REPRESSOR MRNA [SPLIT]_b___b___b___b___>
 <___a_1160__a___a_903 TO 1526 OF TRN10TETR__a_1130__a___a___

410           420           430           440           450
       *             *             *             *             *

GCT GTG GGG CAT TTT ACT TTA GGT TGC GTA TTG GAA GAT CAA GAG
    A   V   G   H   F   T   L   G   C   V   L   E   D   Q   E
  ___TETRACYCLINE REPRESSOR PROTEIN (TETR); CODON START=1____>
  __b___b___b___TETR REPRESSOR MRNA [SPLIT]_b___b___b___b___>
 <1120_a___a___1110_903 TO 1526 OF TRN10TETR_0_a___a___1080a___
```

FIG. 5B

```
       460          470          480          490
        *            *            *            *
CAT CAA GTC GCT AAA GAA GAA AGG GAA ACA CCT ACT ACT GAT AGT
 H   Q   V   A   K   E   E   R   E   T   P   T   T   D   S
___TETRACYCLINE REPRESSOR PROTEIN (TETR); CODON_START=1___>
___b___b___b___TETR REPRESSOR MRNA [SPLIT]_b___b___b___b___>
<___a_1070__a___a_903 TO 1526 OF TRN10TETR__a_1040__a___a___

500          510          520          530          540
        *            *            *            *            *
ATG CCG CCA TTA TTA CGA CAA GCT ATC GAA TTA TTT GAT CAC CAA
 M   P   P   L   L   R   Q   A   I   E   L   F   D   H   Q>
   TETRACYCLINE REPRESSOR PROTEIN (TETR); CODON_START=1___>
___b___b___b___TETR REPRESSOR MRNA [SPLIT]_b___b___b___b___>
<1030_a___a___1020_903 TO 1526 OF TRN10TETR_0_a___a___a990a___

550          560          570          580
        *            *            *            *
GGT GCA GAG CCA GCC TTC TTA TTC GGC CTT GAA TTG ATC ATA TGC
 G   A   E   P   A   F   L   F   G   L   E   L   I   I   C>
___TETRACYCLINE REPRESSOR PROTEIN (TETR); CODON_START=1___>
___b___b___b___TETR REPRESSOR MRNA [SPLIT]_b___b___b___b___>
<___a_980___a___a_903 TO 1526 OF TRN10TETR__a___950__a___a___

590          600          610          620
        *            *            *            *
GGA TTA GAA AAA CAA CTT AAA TGT GAA AGT GGG TCT TAA   (SEQ ID NO: 5)
 G   L   E   K   Q   L   K   C   E   S   G   S   *>  (SEQ ID NO: 6)
___TETRACYCLINE REPRESSOR PROTEIN (TETR); CODON___>
___b___b___TETR REPRESSOR MRNA [SPLIT]_b___b___b___>
<940_a___a___903 TO 1526 OF TRN10TETR___910_a___a___
```

*FIG. 5C*

CHICK β-ACTIN                    *
GGCCCTATAAAAAGCGAAGCGCGCGGCGGGCGGGGGAGTCGCTGCGTTG
         CTTCGCCCCGTGCCCCGCTCCGCCGCCGCCTCCGCCGCCCCGCC    (SEQ. ID NO: 7)
(NON-SPECIFIC EXPRESSION IN MOST TISSUES)
KOST TA., THEODORAKIS N., AND HUGHES SH. (1983) NUCLEIC ACIDS RES. 11;8287-8301

MOUSE ALBUMIN           *
AAGAAGTATATTAGAGCGGAGTCTTTCTGCACACAGATCACCTTTCCTATCAACCCCACTA (SEQ ID NO: 8)
(LIVER SPECIFIC)
GORSKI K., CARNEIRO M., AND SCHIBLER U. (1986) CELL 62;991-998

HUMAN CD-2           *                                                *
GTATTATGTTTTATGTTACTGTAAAAGATGTAAAGAGAGGCACGTGGTTAAGCTCTCGGGGTGTGACTCCACC (SEQ 10 NO: 9)
(T-CELLS)
LANG G., WOTTON D., OWEN MJ., SEWELL WA., BROWN MH., MASON DY., CRUMPTON MJ., AND KIOUSSIS D. 91988) EMBO J. 7; 1675-1682.

HUMAN ALPHA-GLOBIN           *         *
CGCCCAAGCATAAACCCTGGCGCGCTCGCGGCCCCGGCCACTCTTCTGGTCCCCAGACTCAGAGAGAACCCA (SEQ ID NO: 10)
(RED BLOOD CELLS)
LIEBHABER SA., GOOSSENS MJ., AND WAI KAN Y. (1980) PROC. NATL. ACAD. SCI. USA. 77;7054-7058

MOUSE CARDIAC MYOSIN HEAVY CHAIN      *
TAGGCAGCAGGCATATGGGATGGGATATAAGGGCTGGAGCACTGAGAGCTGTCAGAGATTCTCCAACCCAG (SEQ ID NO: 11)
(HEART)
TANIGAWA G., JARCHO JA., KASS S., SOLOMON SD., VOSBERG H.-P., SEDMAN JG., AND SEDMAN CE. (1990) CELL 62;991-998

FIG. 6

FIG. 7

| CONSTRUCT | NT | Hc9-4 | Lc | 4-2 | 2-1 | 2-5 | 7-2 | | NT | Hc | Lc |
|---|---|---|---|---|---|---|---|---|---|---|---|
| ANTIBIOTIC | + - | + - | + - | + - | + - | + - | + - | | + - | + + - | + - - - |
| | | 252 | 252 | 252 | 261 | 261 | 251 | | | 252 9-4 | |

| FOUNDER | 32 | 33 | 31 | | 14 | 19 | 63 | 63 | 44 | 54 |
|---|---|---|---|---|---|---|---|---|---|---|
| TETRACYCLINE | − | − | + | − | + | − | + | − | + | − | + | − | + | − | + | − | + |

FIG. 11

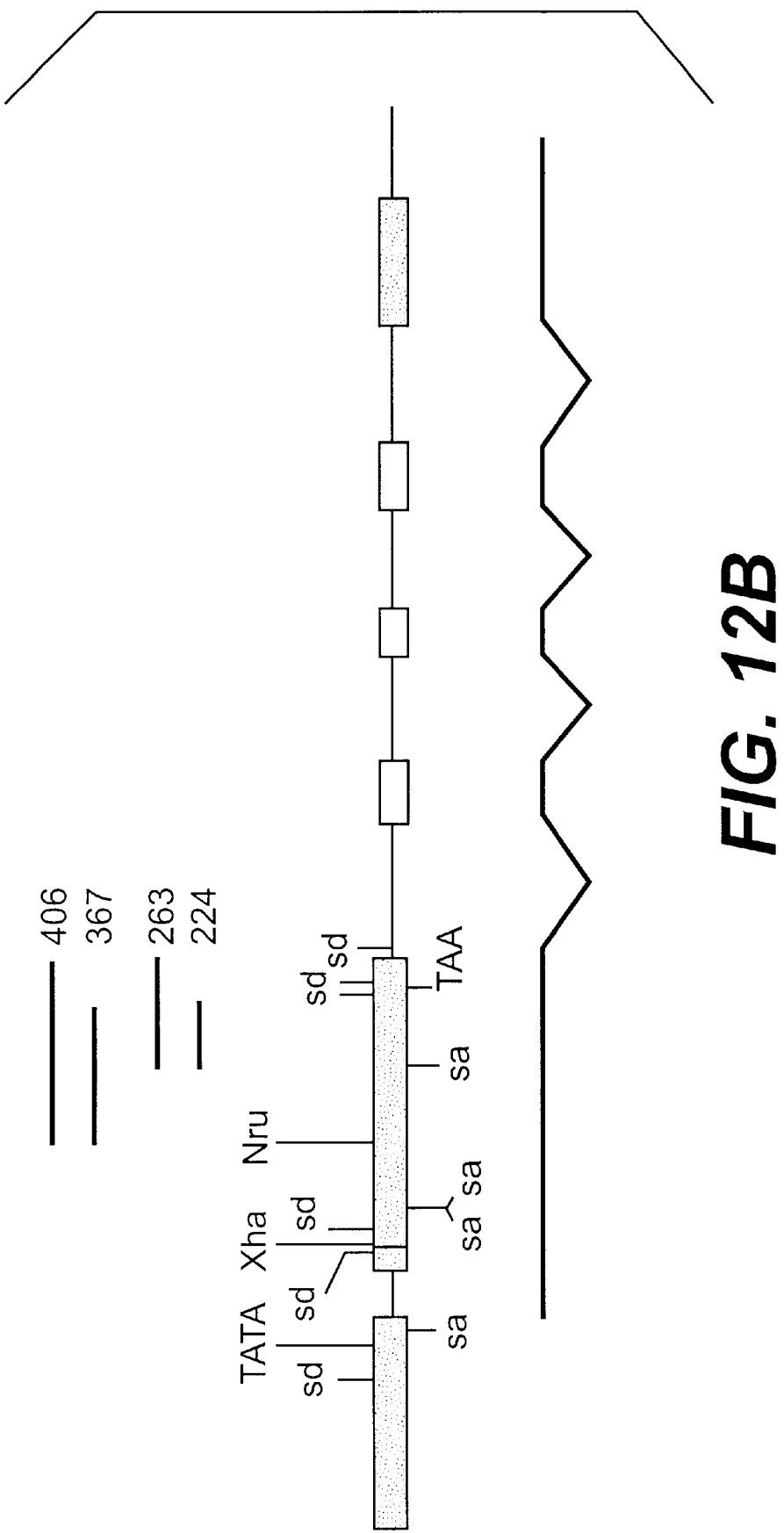

LT-1

EcoR5 AND EcoR1
GATATCGAATTCATGAGTAGATTGGACAAGAGCAAAGTGATCAATAGTGC
TCTGGAGCTGTTGAATGAAGTGGGCATAGAAGGTCTGACTACCAGAAAGC
TGGCCCAGAAGCTGGGAGTGGAGCAGCCAACATTGTACTGGCATGTGAAG
AATAAGAGGGCTCTGCTGGATGCATTGGCGGTACCAGGC(SEQ ID NO:16)
                    Nsi1        Kpn1

LT-2
    Kpn1      Nsi1
GCTCGGTACCTGGATGCATTGGCCATTGAGATGCTGGACAGACACCATAC
ACACTTCTGCCCACTGGAAGGCGAGAGTTGGCAGGACTTCCTGAGGAACA
ATGCTAAGAGTTTCAGATGTGCTCTGTTGAGCCACAGAGACGGTGCTAAA
GTGCACCTGGAATTCGAGC (SEQ ID NO:17)
 ApaL1     EcoR1

LT-3
     EcoR1     ApaL1
GCTCGAATTCAAAGTGCACCTGGGTACAAGGCCAACAGAGAAACAGTACG
AGACCCTGGAGAACCAGCTGGCATTTCTGTGCCAACAAGGCTTCAGCCTG
GAGAATGCATTGTATGCTCTGAGTGCTGTGGGTCACTTCACACTGGGTTG
TCTCCTGGAGGACCAGGAGCACCAGGTGGCCAAGGAGGAGAGGGAGACCC
CAACCACTGACAGCATGCCCCGGATCCGAGC (SEQ ID NO:18)
             Sph1       BanH1

LT-5
    BamH1      Sph1
GCTCGGATCCACAGCATGCCCCCATTGCTGAGACAGGCCTATGAGCTGTT
TGACCACCAAGGGGCAGAGCCTGCTTTTCTGTTTGGCCTGGAGCTCATCA
TCTGTGGTCTGGAGAAGCAGCTGAAGTGTGAGAGTGGCTCCTGAAGCTTG
ATATC (SEQ ID NO:19)                        Hind3/EcoR5

FIG. 15

```
GATATCGAAT  TCATGAGTAG  ATTGGACAAG  AGCAAAGTGA
TCAATAGTGC  TCTGGAGCTG  TTGAATGAAG  TGGGCATAGA
AGGTCTGACT  ACCAGAAAGC  TGGCCCAGAA  GCTGGGAGTG
GAGCAGCCAA  CATTGTACTG  GCATGTGAAG  AATAAGAGGG
CTCTGCTGGA  TGCATTGGCC  ATTGAGATGC  TGGACAGACA
CCATACACAC  TTCTGCCCAC  TGGAAGGCGA  GAGTTGGCAG
GACTTCCTGA  GGAACAATGC  TAAGAGTTTC  AGATGTGCTC
TGTTGAGCCA  CAGAGACGGT  GCTAAAGTGC  ACCTGGGTAC
AAGGCCAACA  GAGAAACAGT  ACGAGACCCT  GGAGAACCAG
CTGGCATTTC  TGTGCCAACA  AGGCTTCAGC  CTGGAGAATG
CATTGTATGC  TCTGAGTGCT  GTGGGTCACT  TCACACTGGG
TTGTGTCCTG  GAGGACCAGG  AGCACCAGGT  GGCCAAGGAG
GAGAGGGAGA  CCCCAACCAC  TGACAGCATG  CCCCCATTGC
TGAGACAGGC  CATAGAGCTG  TTTGACCACC  AAGGGGCAGA
GCCTGCTTTT  CTGTTTGGCC  TGGAGCTCAT  CATCTGTGGT
CTGGAGAAGC  AGCTGAAGTG  TGAGAGTGGC  TCCTGAAGCT
TGATATC
```

(SEQ ID NO:20)

*FIG. 16*

TETRACYCLINE REPRESSOR-MEDIATED BINARY REGULATION SYSTEM FOR CONTROL OF GENE EXPRESSION IN TRANSGENIC MICE

This 371 application claims the benefit of PCT/US93/08230, filed Aug. 26, 1993, which is a continuation-in-part of U.S. Application Ser. No. 07/935,763, filed Aug. 26, 1992, now abandoned.

1. INTRODUCTION

The present invention relates to a tetracycline repressor-mediated binary regulation system for the control of gene expression in transgenic animals. It is based, at least in part, on the discovery that, in a non-human transgenic animal that carries a first transgene under the control of a modified promoter comprising a tetR operator sequence and a second transgene encoding the tetR repressor protein, expression of the first transgene may be efficiently induced by administering tetracycline to the animal.

2. BACKGROUND OF THE INVENTION

2.1. Control of Gene Expression in Transgenic Animals

The production of transgenic animals for both experiment and agricultural purposes is now well known (Wilmut et al., Jul. 7, 1988, New Scientist pp. 56–59). In research, transgenic animals are a powerful tool that have made significant contributions to our understanding of many aspects of biology and have contributed to the development of animal models for human diseases (Jaenisch, 1988, Science 240:1468–1474). It is also clear that several livestock species can be made transgenic and these species promise to expand and revolutionize the method of production and diversity of pharmaceutical products available in the future, in addition to improving the agricultural qualities of the livestock species (Wilmut et al., supra).

A critical, often neglected, aspect of developing transgenic animals is the process whereby expression of the newly introduced gene, referred to as the transgene, is controlled. This is an important process since stringent regulation of transgene expression is often important both for practical, regulatory and safety reasons and to maintain the health of the transgenic animal. In the past either "inducible" or "tissue specific" regulatory mechanisms have been used. Inducible regulation is defined herein as a method of gene regulation which allows for some form of outside manipulation of the onset and/or level of transgene expression. Tissue specific regulation is defined herein as a method for targeting transgene expression to particular tissues or organs.

Inducible gene regulation may be achieved using relatively simple promoter systems such as the metallothionein heat shock promoters, or by using promoters which are responsive to specific compounds such as the Mouse mammary tumor virus LTR which is responsive to glucocorticoid stimulation. More flexible, though more complex inducible regulation systems can be achieved through a "binary" gene approach which utilizes a transactivator gene product to control expression of a second gene of interest. Tissue specific gene regulation usually consists of simple single gene methods (Byrne et al., 1989, Proc. Natl. Acad. Sci. U.S.A. 86:5473–5477; Ornitz et al., 1991, Proc. Natl. Acad. Sci. U.S.A. 88:698–702), although binary transactivator systems can also provide a high degree of tissue specificity.

These current systems provide only a limited ability to control the time of transgene expression within individual animals. In this respect tissue specific promoter elements provide no method to control the onset of transgene activity, but function merely to target gene expression to defined sites. Simple inducible promoters such as metallothionein generally lack tissue specificity and usually have some aspect of endogenous basal expression which cannot be controlled. Thus even for the extensively used inducible metallothionein promoter this approach at best only permits selection of the time at which a relative increase in transgene expression can be induced.

Binary transactivation systems typically consist of two transgenic animals. One animal contains the gene of interest controlled by a promoter element that requires a specific transactivator gene product for expression. Thus, the gene of interest is not expressed in the absence of the transactivator. A second transgenic animal is then made which expresses the required transactivator in the desired tissue. By mating these two transgenic animals, offspring containing both the gene of interest and the transactivator transgene can be produced. Only in these doubly transgenic animals is the gene of interest expressed. Since expression of the gene of interest requires the transactivator, this binary approach dramatically reduces or eliminates any undesirable basal expression inherent in simple inducible systems. Additionally, if expression of the transactivator is targeted using a tissue specific promoter, then in the double transgenics, expression of the gene of interest is in effect targeted to the same specific tissue. Binary systems provide therefore a low resolution method of temporal regulation in as much as they allow the determination of which generation of animals will express the gene of interest. These systems provide little ability, however, to control the time and level of gene expression within an individual transgenic animal.

For many applications it is necessary to accurately control the time and pattern of transgene expression within an individual transgenic animal. For example, many attempts have been made to produce transgenic pigs which express increased levels of growth hormone (Vize et al., 1988, J. Cell Sci. 90:295–300; Pinkert et al., 1990, Dom. Animal Endocrinol. 7:1–18). Elevated growth hormone levels dramatically decrease the amount of body fat in pigs, and increase the animals overall feed efficiency. These effects would be beneficial, both to the consumer who could purchase a leaner, healthier product, and to the producer who can profit from having a more efficient animal. To date however, all attempts to increase the level of growth hormone through production of transgenic pigs have also produced serious pathological conditions which greatly reduce the health of the animals. These pathologies are the direct result of uncontrolled, constitutive expression of growth hormone, since many studies using exogenous hormone administration for short periods of time have not produced pathologies, while still benefiting feed efficiency and fat content. In this situation, a regulatory method to control onset and level of expression from a growth hormone transgene would be extremely useful.

2.2. Repressor-Mediated Gene Control

Transcriptional repressors are usually allosteric DNA binding proteins with at least two functional sites. One site on the protein is used to bind DNA. The DNA binding site binds to a defined DNA sequence which is known as the operator site. Operator sites usually consist of palindromic sequences of 12 or more base pairs. A gene which is regulated by a repressor must have at least one operator site located within its promoter/regulatory region. A second site on the repressor protein binds a specific ligand, usually a small macromolecule such as an amino acid, sugar, or antibiotic. When the ligand is bound to the repressor, it causes a conformational shift such that the affinity of the repressor for the operator sequence is greatly reduced. For this reason, the ligand is frequently referred to as the "inducer", since it causes the repressor to disassociate from the operator, thereby eliminating the repressor's effect and allowing expression of the gene.

Only the bacterial repressors LacI, LexA and tetR have been shown to function in mammalian (LacI and LexA) or plant (tetR) tissue culture cells. The first report of utilizing bacterial repressors in eukaryotes was from Brent and Ptashne who showed that LexA could function in yeast (1984, Nature 312:612–615). Subsequently, both LexA and LacI have been shown to function in mammalian tissue culture systems (Smith et al., 1988, EMBO J. 7:3975–3981). Of these repressors LacI has been most extensively studied. For LacI repression, single or multiple operator sites have been positioned in three major locations: (i) between the transcription start site and the first codon of the mRNA; (ii) between the TATA-box sequence and the transcription start site; and (iii) between the TATA-box sequence and any more distal regulatory signal sequences. These studies reveal two predominant results. First, operators located in all three positions were effective in rendering the modified promoter subject to LacI repression. Second, the presence of multiple operator sequences allowed greater levels of repression than did single operator insertions. From these studies it appears the LacI repressor causes repression of mammalian promoters through two basic mechanisms. If the operators are located downstream of the transcription start site, LacI appears to block expression by inhibiting mRNA elongation. That is to say, the LacI repressor blocks the progress of RNA polymerase by steric interference. When operator sequences are located in other positions, LacI seems to inhibit protein-protein interactions between the cellular factors normally involved in transcription initiation.

Gatz and Quail (1988, Proc. Natl. Acad. Sci. U.S.A. 85:1394–1397) have demonstrated tetR function in a plant protoplast culture system. Plant protoplasts were transfected with a tetR gene expressed from a cauliflower mosaic virus (CAMV) promoter along with a CAT reporter gene, regulated by a modified CAMV promoter. In contrast to the results with LacI, Gatz and Quail showed that tetR operators positioned between the transcription start site and the first codon of the CAT mRNA were not responsive to tetR repression. Therefore the tetR protein does not appear to be able to block the procession of RNA polymerase. Effective repression by tetR was only observed when the operator sequence was positioned such that the CAMV TATA-box element was flanked by the two 19 palindromes of the tetR operator. With this modification, effective repression of the reporter gene, and induction with tetracycline could be achieved. This suggests that repression by tetR specifically inhibits the initiation of transcription, in this case apparently by blocking the binding of the TATA-box binding factors.

Recently the tetR system has been shown to function in transgenic plants. Gatz et al. (1991, Mol. Gen. Genet. 227:229–237) have introduced their original tetR responsive CAMV promoter, in which the operator sites flank the TATA-box into transgenic tobacco plants. Unexpectedly, this promoter, which exhibited very good regulation in tissue culture assays was not very effective in regulating gene expression in transgenic plants. Instead they found that effective repression and induction in transgenic plants occurred when the operator sites were positioned just downstream of the normal transcription start site.

3. SUMMARY OF THE INVENTION

The present invention relates to a tetracycline repressor-mediated binary regulation system for the control of gene expression in non-human transgenic animals. It is based, at least in part, on the discovery that in transgenic mice carrying two transgenes, the first encoding bovine growth hormone (bGH) under the control of a PEPCK promoter modified to comprise the tetR operator sequence at the NheI site, and the second encoding tetR repressor protein under the control of an unmodified PEPCK promoter, expression of bGH could be efficiently and selectively induced by administering tetracycline to the transgenic mice.

In particular embodiments, the present invention provides for (i) animal promoter elements modified to comprise a tetR operator sequence; (ii) nucleic acid molecules comprising a gene of interest under the control of such a modified promoter; (iii) non-human transgenic animals that carry a transgene under the control of said modified promoter and/or a transgene encoding the tetR repressor protein; and (iv) a method of selectively inducing the expression of a gene of interest in a non-human transgenic animal comprising administering tetracycline to a non-human transgenic animal that carries a first transgene, which is the gene of interest under the control of a promoter modified to comprise a tetR operator sequence and a second transgene encoding the tetR repressor protein.

The present invention offers the advantage that, in the absence of tetracycline, expression of the gene of interest occurs at only very low levels due to efficient repression by tetR. In preferred, non-limiting embodiments of the invention, repression by tetR is further enhanced by utilizing a synthetic tetR gene which is devoid of splice signals and has optimized codon usage for mammalian cells. Accordingly, the present invention allows tight control of gene expression in transgenic animals by withholding or administering tetracycline.

4. DESCRIPTION OF THE FIGURES

FIG. 1. A. Nucleotide sequence of tetR operator as it occurs in Tn10 (SEQ ID NO:1), and in the oligonucleotides used to produce the modified PEPCK promoter elements (SEQ ID NO:2). Bold face lettering represent the OP1 and OP2 tetR binding sites. The general purpose oligonucleotide (SEQ ID NO:2) is the sequence from p∂∂7. The flanking EcoRI and AccI restriction sites used to excise this operator sequence are indicated. Additional restriction sites present in the plasmid, but not indicated here, which can be used to excise the operator (SEQ ID NO:3) include PstI, BamHI, SpeI, SbaI, NotI, EagI, SacII, BstXI, and SacI on the 5' side and XhoI, ApaI and KpnI on the 3' side. The sequence of the PEPCK-TATA box operator is also indicated (see methods) (SEQ ID NO:3).

FIG. 1. B. Nucleotide sequence of the ∂∂7 operator (SEQ ID NO:4). Lower case letters correspond to polylinker sequence. The 5' EcoRI and 3' AccI restriction sites used for producing the modified PEPCK promoters (Pck_A and Pck-N) are indicated. The 10 base pair linker beween OP1 and OP2 is underlined. Additional polylinker restriction sites available in p∂∂7 include PstI, BamHI, SpeI, XbaI, NotI, EagI, SacII, BstXI, and SacI on the 5' side and XhoI, ApaI and KpnI on the 3' side.

FIG. 2. A representation of the three modified PEPCK promoter elements. Construct 251 has the ∂∂7 operator sequence integrated in the AccI site of PEPCK, just 5' of the TATA-box control element. Construct 252 has the ∂∂7 operator sequence incorporated into the NheI site of PEPCK, just 3' of the TATA-box element. Construct 261 incorporates the TATA-specific operator sequence which is integrated between the 5' AccI site and the 3' NheI sites.

Figure 3A:
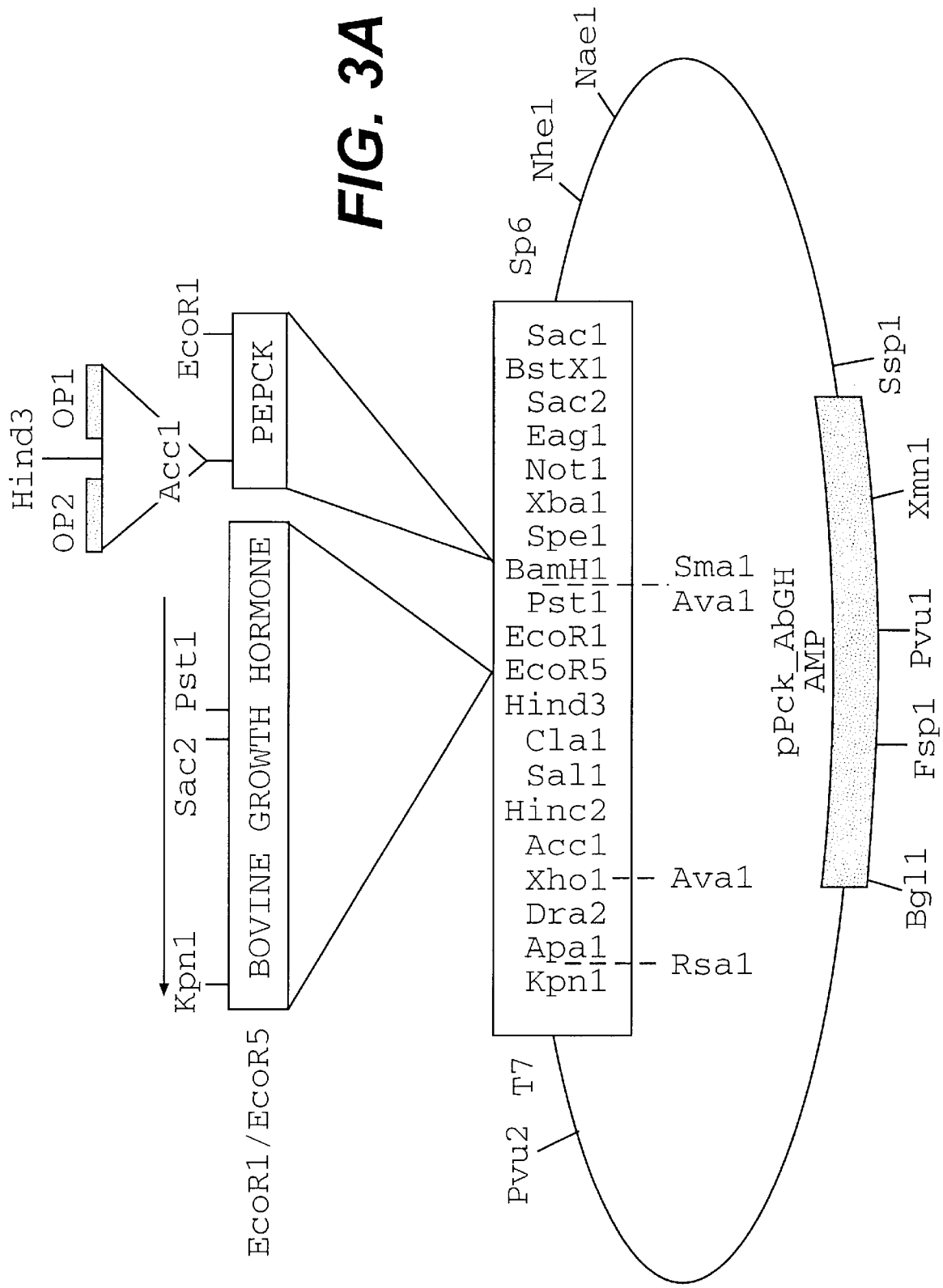
Figure 3B:
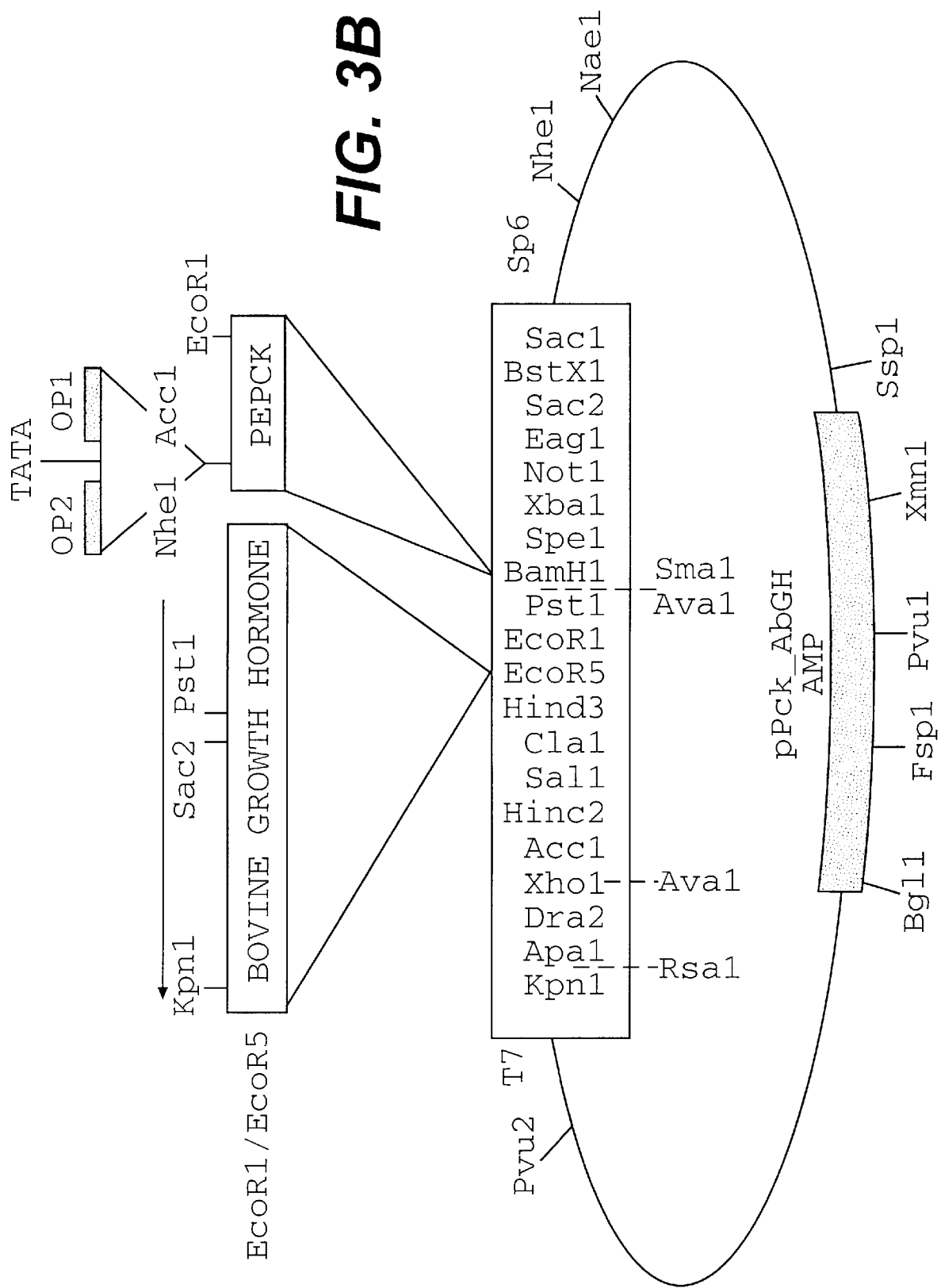
Figure 3C:
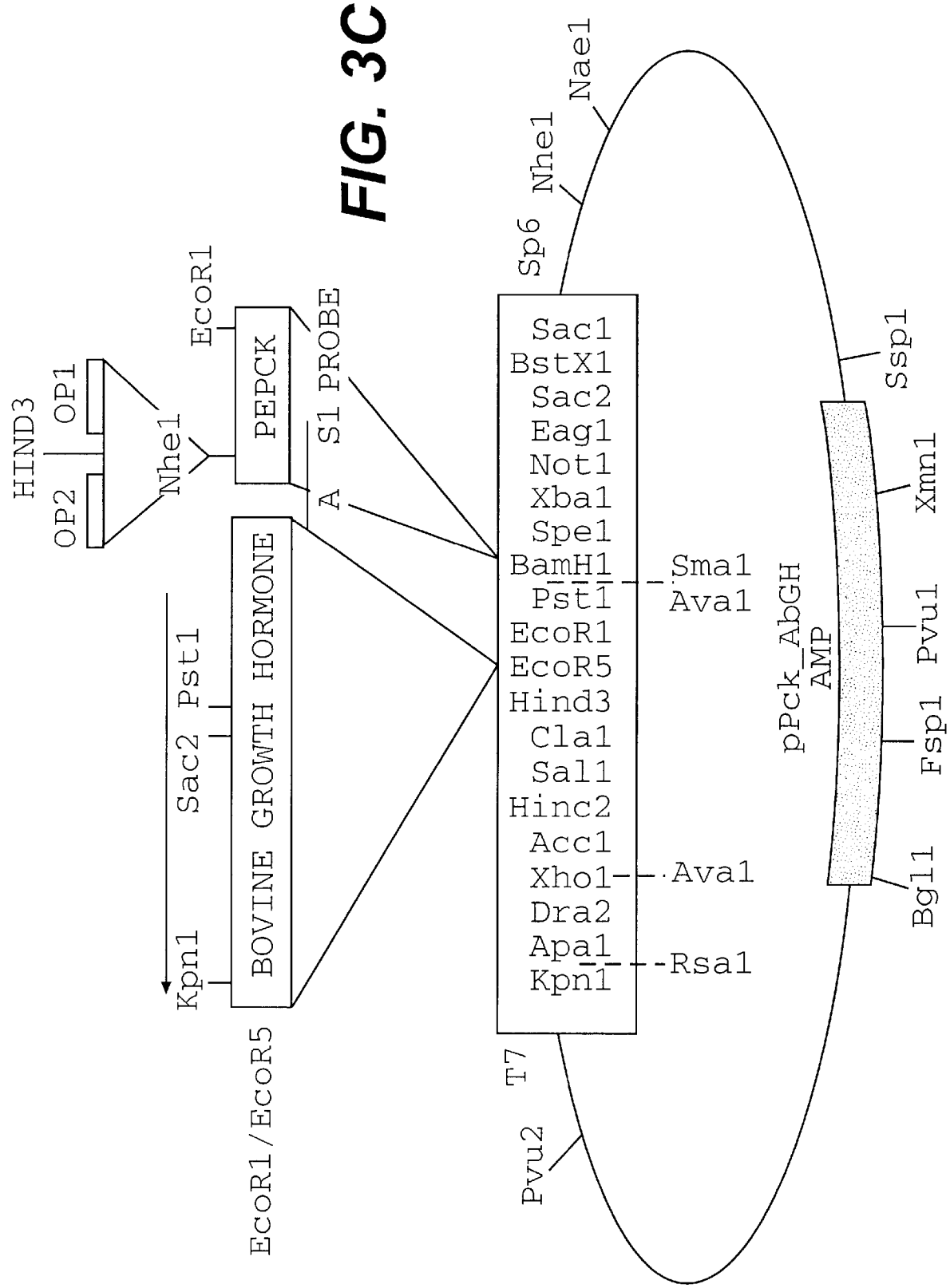

FIG. 3. Structure of the modified PEPCK controlled bovine growth hormone genes. The Pck__AbGH and Pck__NbGH genes differ only in the site of operator insertion. For Pck__AbGH the operator is inserted at the AccI site 5' of the PEPCK TATA-box element. For Pck__NbGH the operator is inserted into the NheI site 3' of the TATA-box element (pPCK__NbGH has been deposited with the ATCC and assigned accession No: 69400). In the Pck__TbGH gene, a TATA-box specific oligonucleotide was used, and this sequence was inserted between both the AccI and NheI sites. A. Indicated the probe used for S1 hybridization.

Figure 4:
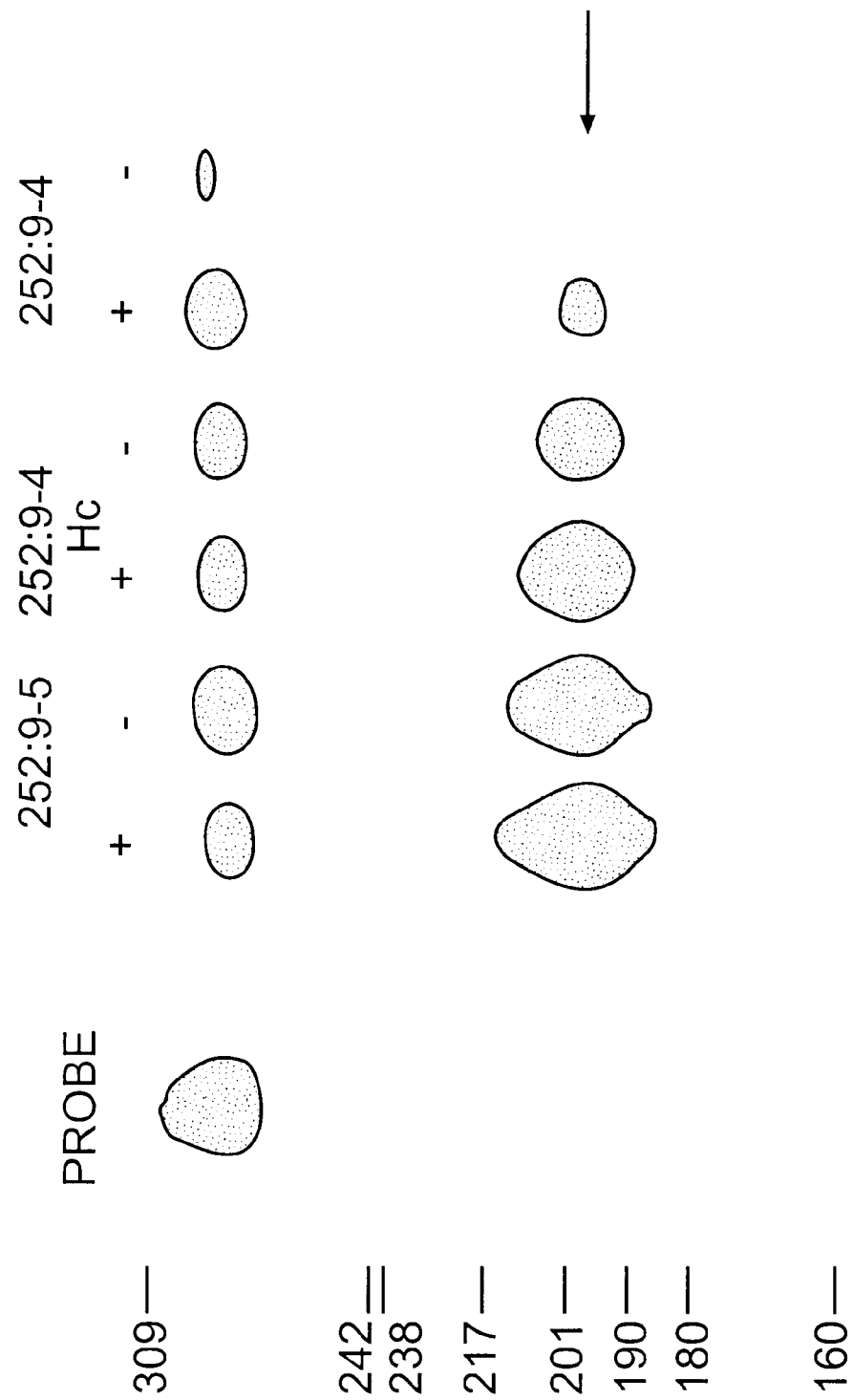

FIG. 4. S1 Nuclease protection assay to map the 5' start site of bGH from the Pck__N promoter. Total liver RNA (10 µg) was hybridized to a 280 bp 5' labelled probe from the Pck__NbGH gene in 40 mM PIPES (Ph6.4), 1 Mm EDTA, 400 mM NaCl, 80% formamide at 55° overnight. The probe spanned from the HinfI site in the 5' untranslated leader sequence of bGH to the PvuII site 5' of the TATA-17 box. The probe includes the tet-operator sequence of Pck__N (see FIG. 3). After hybridization 300 µl of ice cold digestion buffer (280 mM NacL, 50 Mm SODIUM ACETATE (Ph4.5), 4.5Mm ZnSO$_4$, 20 µg/ml carrier DNA and 500 units S1 nuclease) was added and incubated at 37° for 30 minutes. The reaction as stopped by adding 80 µl of Stop Buffer (4M Ammonium acetate, 50 mM EDTA and 50 µg/ml tRNA), extracted with phenol/chloroform, precipitated with ethanol and analyzed on a 6% sequencing gel. The arrow indicates the protected fragment. Initiation of bGH mRNA from the modified Pck__N promoter occurs approximately 20 bp 3' of the TATA-box. This initiation site places the start of the message just prior to the first tetR binding site. This result indicates that the bGH mRNA starts from a single cap site, and suggests that tetR repression is due to a block in transcription initiation. Furthermore, unrepressed bGH expression appears to be due to limited tetR expression.

FIG. 5. Nucleotide sequence (SEQ ID NO:5) of the tetR repressor protein (SEQ ID NO:6) gene.

FIG. 6. Alterative, nonlimiting promoters of interest (Chick β-actin:SEQ ID NO:7; Mouse Albumin:SEQ ID NO:8; Human CD-2:SEQ ID NO:9; Human alpha-globin:SEQ ID NO:10; Mouse Cardiac Myosin Heavy Chain:SEQ ID NO:11). Asterisks indicate sites at which tetR operator sequence may be inserted.

FIG. 7. Northern blot analysis of bGH mRNA in liver of F1 generation animals.

Figure 8:
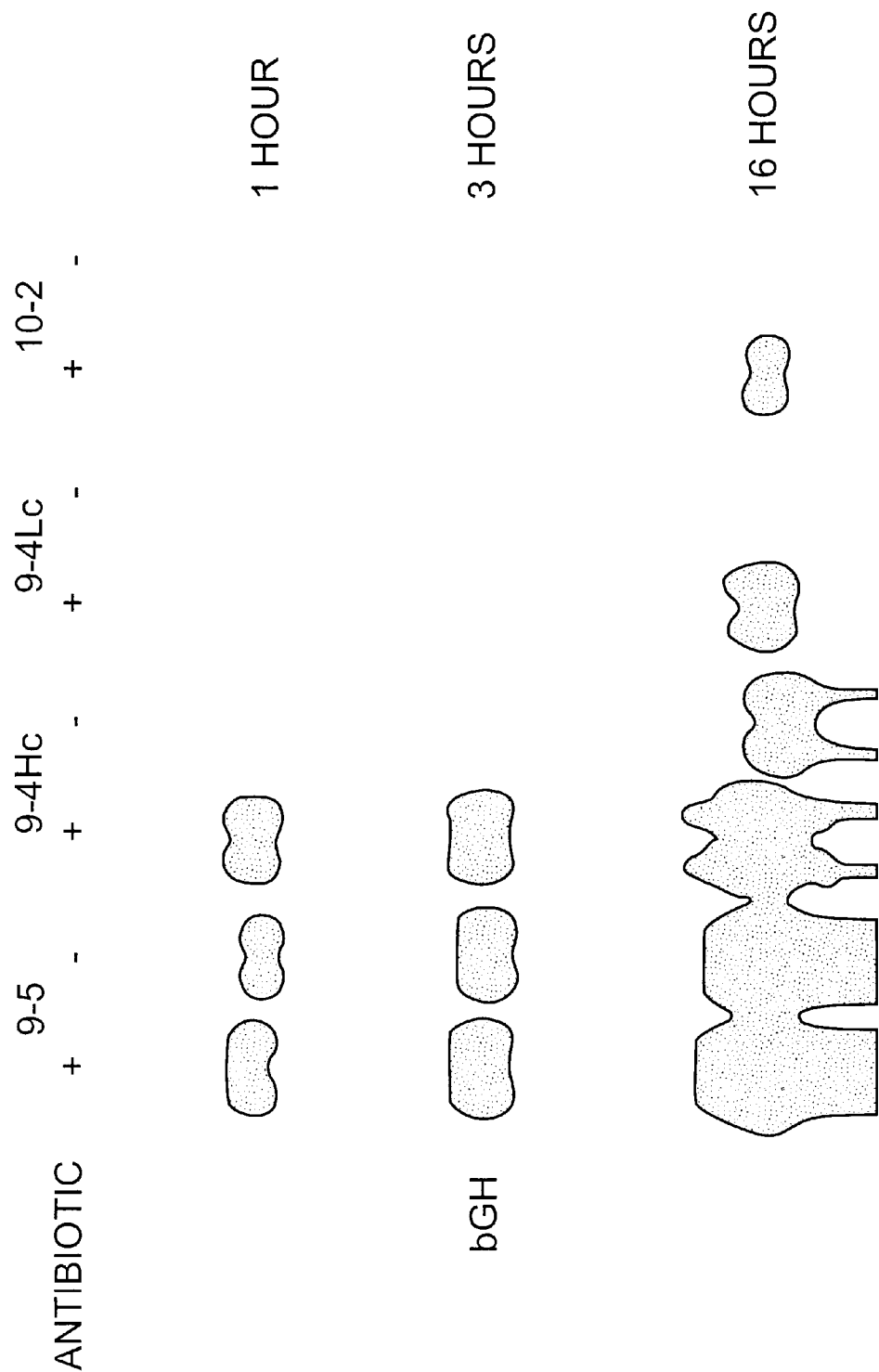

FIG. 8. Northern blot analysis of bGH mRNA expression in four transgenic lines.

Figures 9A, 9B:
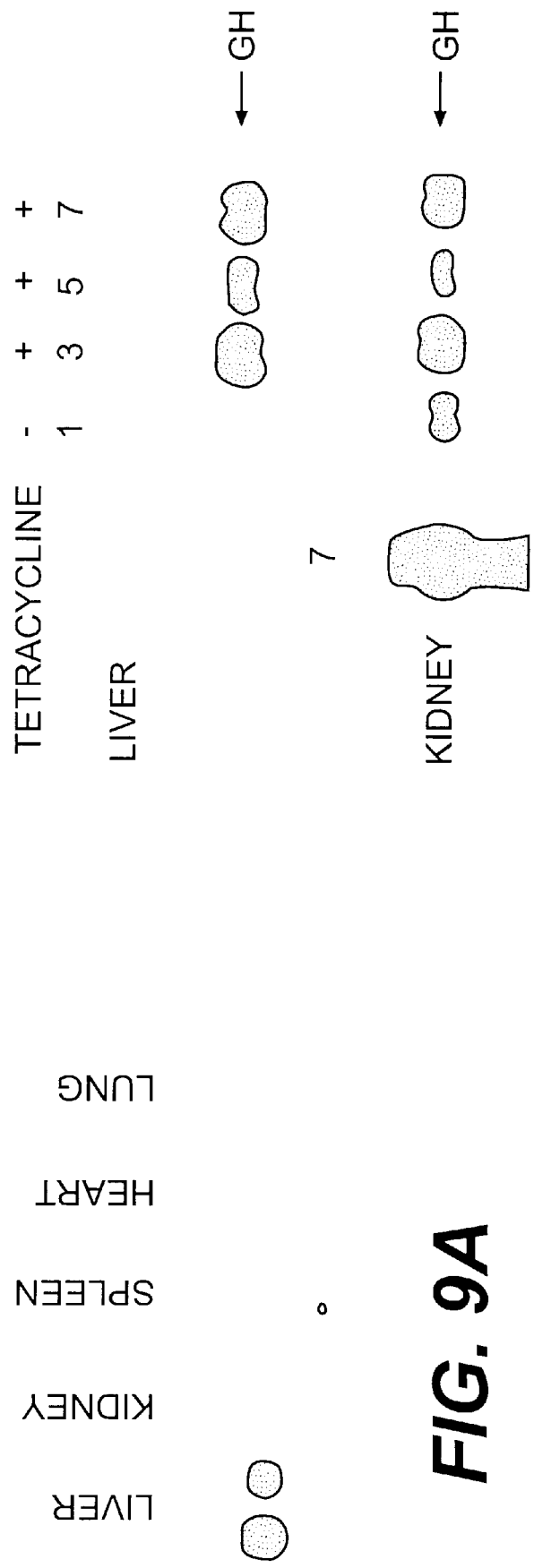

FIG. 9A. Tissue specificity of bGH expression in Line 10-2 in the presence of 50 µg/ml tetracycline. Northern blot analysis of bGH induction in a variety of tissues. Only the liver and kidney show significant expression.

FIG. 9B. Tetracycline induction of bGH in Line 10-2. Both liver and kidney, which are the only sites for bGH expression in FIG. 9A, also show tetracycline dependent bGH expression.

Figure 10:
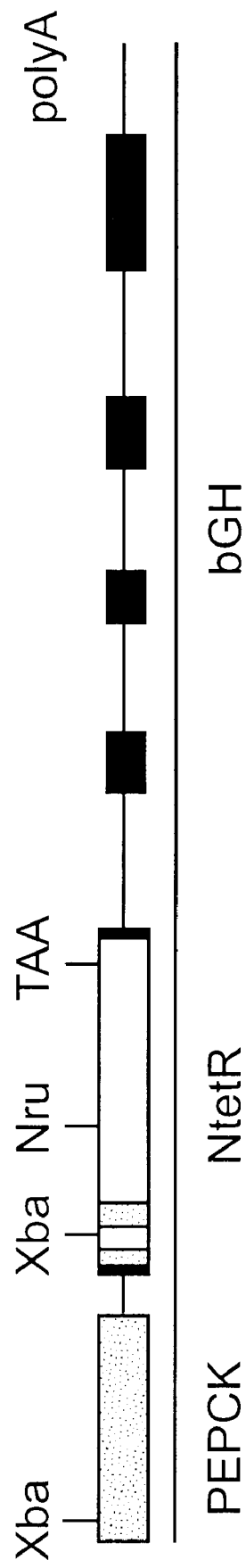

FIG. 10. 345 Repressor Construct.

Figure 11:
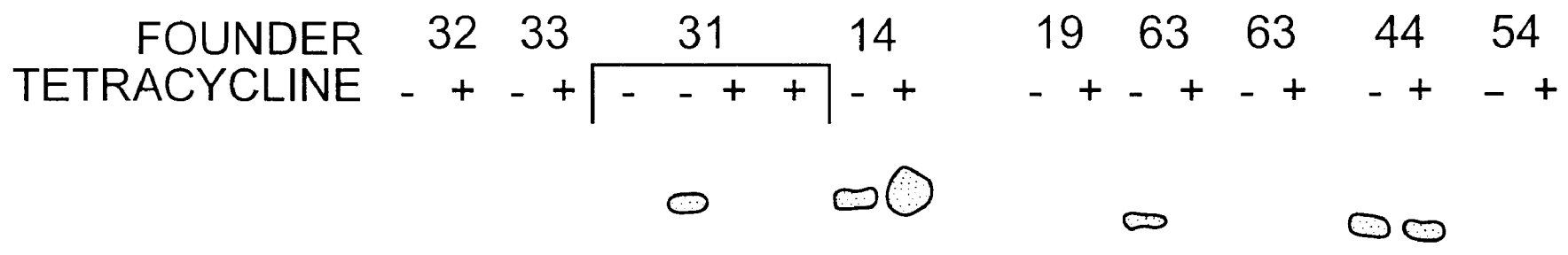

FIG. 11. Induction of bGH expression in Construct 345 Offspring. Northern blot analysis of liver RNA from F1 animals containing the 345 construct. Only animals from line 14 exhibit tetracycline dependent bGH expression.

Figure 12A:
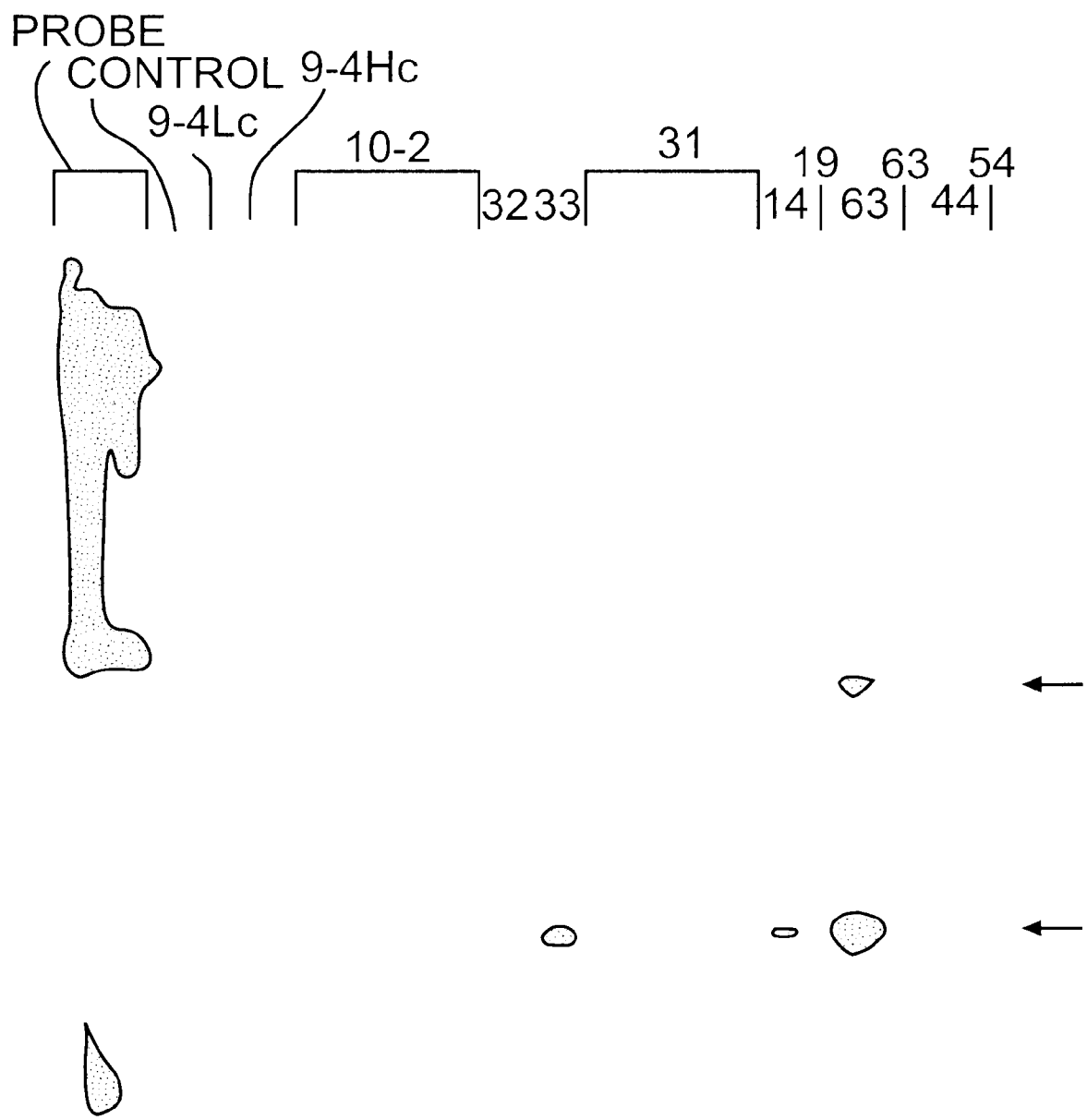

FIG. 12. Expression and alternative processing of tetR transgene. A RNase protection probe which extends from the NruI site of tetR 3' to the end of the gene was used. This probe includes only tetR coding sequences and should give a fully protected fragment of approximately 400 base pairs. A protected fragment of approximately 220–260 base pairs is observed, which is far smaller then predicted.

Figure 13:
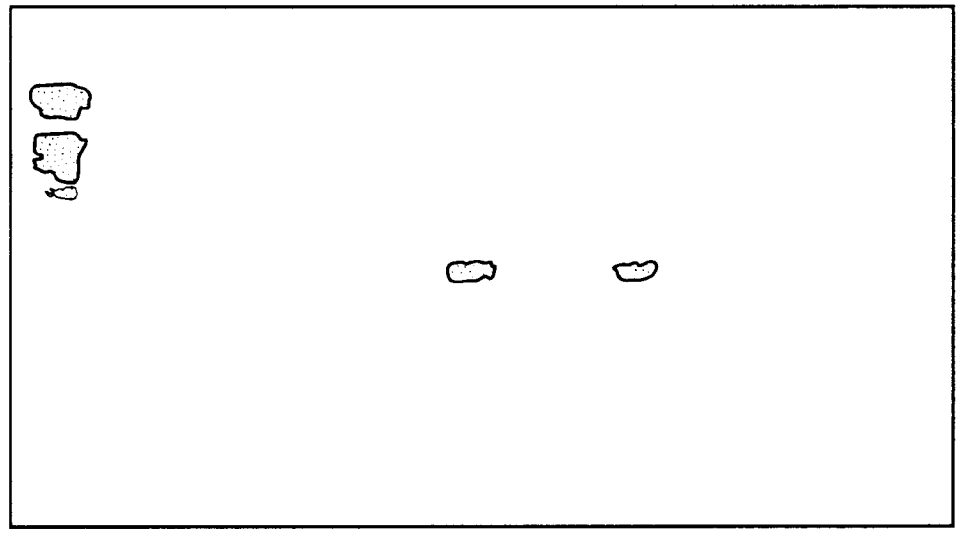

FIG. 13. 5' Structure of tetR mRNA. Liver RNA was treated with reverse transcriptase and amplified by PCR. The RNA was amplified using two different pairs of primers. The first primer pair (TZ-1 and TZ-4) should produce a 619 base pair product. The second primer pair (TZ03 and TZ04) should produce a 498 base pair product. The sequence of the primers are:

TZ-1(SEQ ID No:21)
:5'CCGCATATGATCAATTCAAGGCCGAATAAG3'
TZ-3(SEQ ID No:22)
:5'CTTTAGCGACTTGATGCTCTTGATCTTCCA3'
TZ-4(SEQ ID No:23)
:5'AATTCGCCAGCCATGCCAAAAAAGAA-GAGG3'

The TZ-4 primer is common to both primer pairs and is the 5' primer which encompasses the start codon of the tetR and mRNA. Primer TZ-1 and TZ-3 are two different 3' primers both of which are in the tetR coding region. When amplified, these primer pairs produced smaller then expected products (approx. 215 bp vs. 619 bp for TZ-4 and TZ-1, and approx. 94 bp vs. 498 bp for TZ-4 and TZ-3). The products of this reaction were cloned and sequenced. Sequencing revealed the presence of an unexpected intron which spanned from near the XbaI site at the start of tetR to a splice acceptor just 8 base pairs 5' of the TZ-3 primer.

Figure 14A:
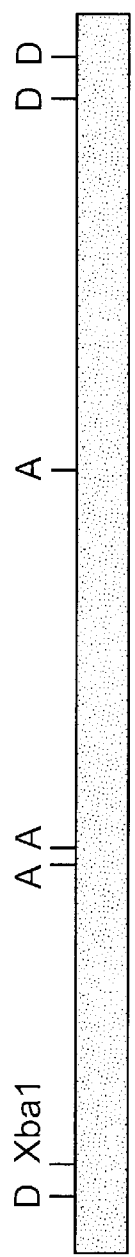
Figure 14B:
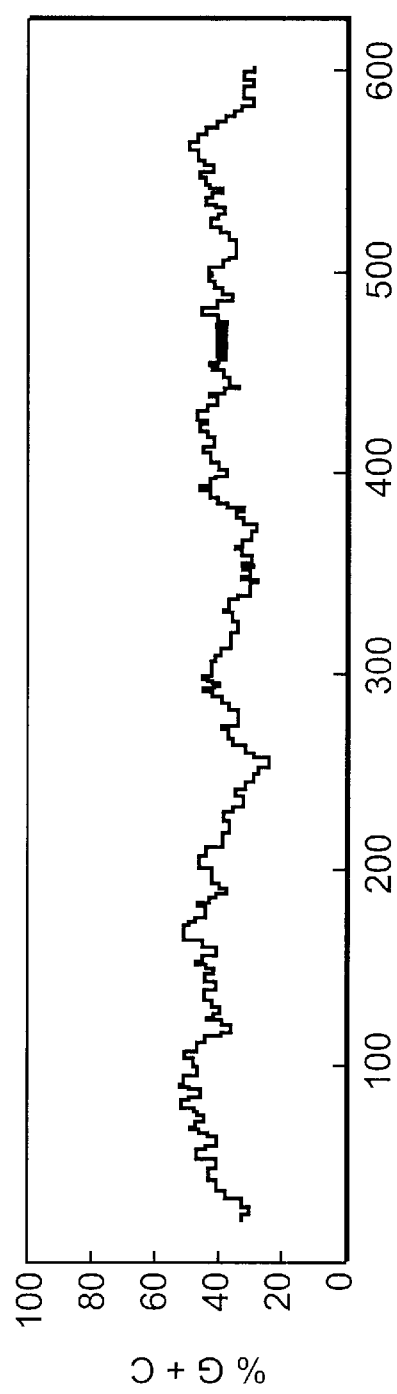
Figure 14C:
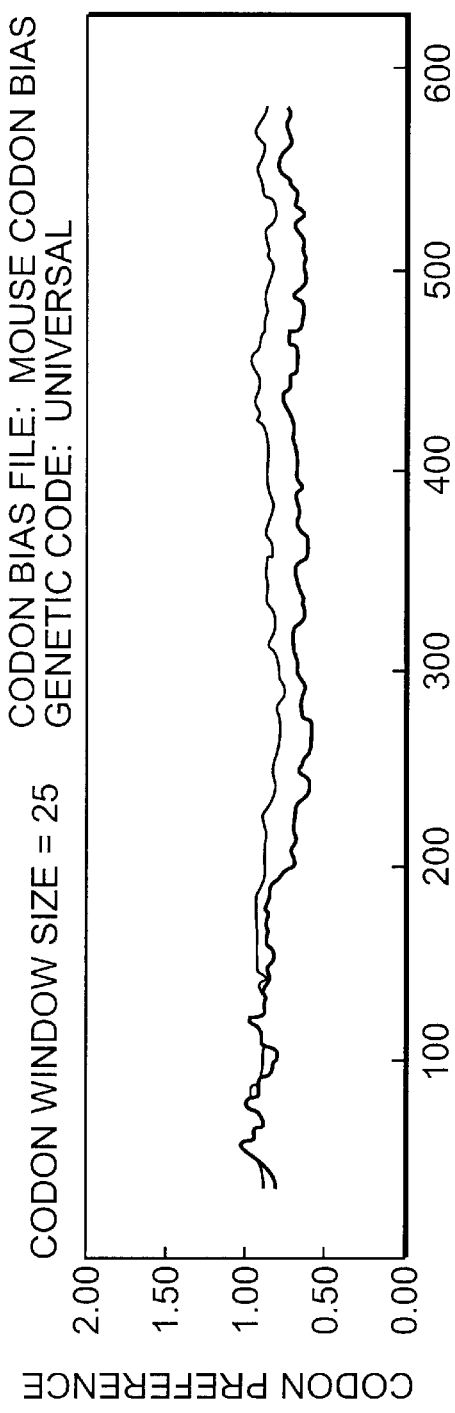

FIG. 14. Composition analysis of Wild Type Tn10 tetR gene. The Tn10 tetR coding sequence was analyzed on a desktop computer using Mac Vector software. The figure shows a diagram of the tetR coding region with the plus strand splice doner (D) and splice acceptor (A) signal sequences indicated. For reference the location of the XbaI restriction is also indicated. The first graph depicts the percentage of G and C bases in the coding region of tetR. There are several domains of very low GC content. The bottom graph is an analysis of codon bias. The dark line is a comparison of the tetR codon usage to a mouse codon bias table. Values lower than 1.0 are indicative of sequences which may translate poorly. For reference, a comparison of tetR to a Tobacco codon bias table is included (light line). In transgenic tobacco, the tetR regulation system functions very efficiently, suggesting that for this gene, codon bias may be an important factor for efficient expression.

FIG. 15. Synthetic tetR Component Sequences (LT-1:SEQ ID NO:16; LT-2:SEQ ID NO:17; LT-3:SEQ ID NO:18; LT-5:SEQ ID NO:19). The components of the synthetic tetR gene were synthesized by Midland Laboratories as four overlapping double stranded DNA cassettes. The sequence of these cassettes are shown. Each cassette was blunt cloned into the Hinc2 site of pUC19 and sequenced to verify authenticity. The resulting plasmids pLT1, pLT2, pLT3 and pLT5 can be used as the source material to assemble the entire synthetic tetR coding sequence since each contains an overlapping unique restriction site (bold face) through which they can be joined.

FIG. 16. Sequence of Synthetic tetR gene (SEQ ID NO:20).

Figure 17A:
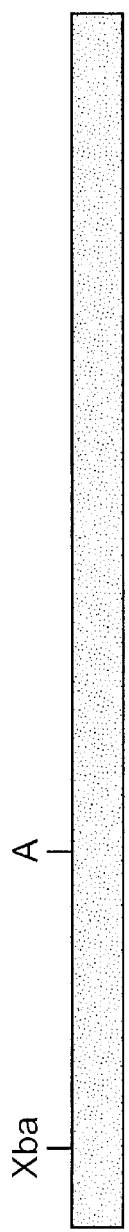
Figure 17B:
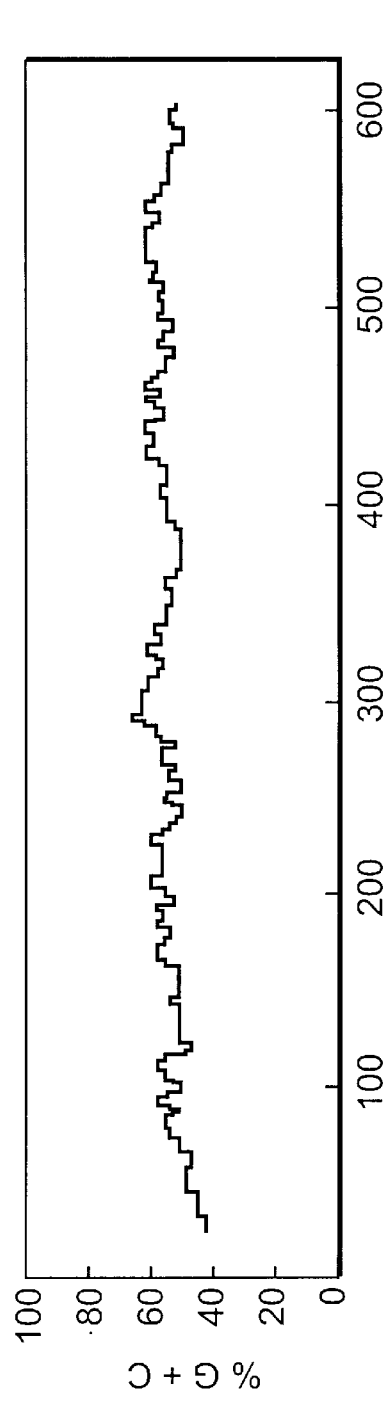
Figure 17C:
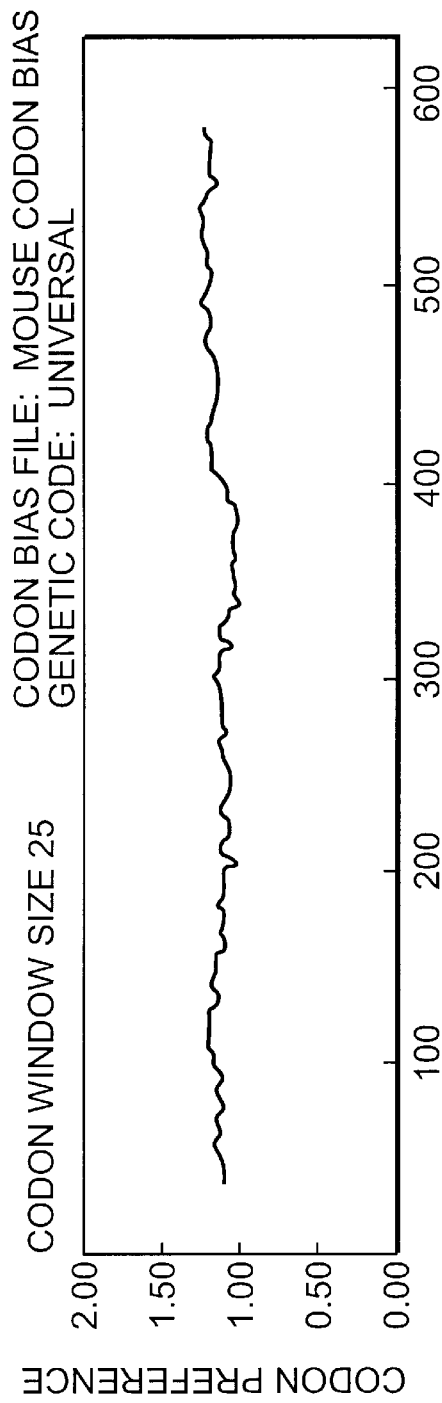

FIG. 17. Composition analysis of synthetic tetR. These graphs were produced using the same software described in FIG. 15. The figure depicts the structure of the synthetic tetR gene, now devoid of splice donor signal sequences, with only a single splice acceptor signal remaining (A). This is not the splice acceptor which was active in the 345 construct. The percentage of G and C bases has been significantly improved, while the frequency of CpG base pairs has been kept to a minimum. A CpG base pair is frequently the site for DNA methylation, which can negatively effect the expression of a gene. The codon bias of the synthetic tetR gene is also vastly improved. The graph depicts the results when the synthetic tetR coding sequence is compared to the same mouse codon bias table used previously.

5. DETAILED DESCRIPTION OF THE INVENTION

For purposes of clarity of description, and not by way of limitation, the detailed description of the invention is divided into the following subsections:

(i) the tetR operator;

(ii) modified promoters containing the tetR operator; and (iii) utility of the invention.

5.1. The TetR Opreator

In order to practice the instant invention, the tetR operator sequence is inserted into a suitable animal promoter sequence in order to render that promoter subject to control by tetR repressor protein. A diagram of the tetR operator sequence is depicted in FIG. 1.

It may be convenient to clone the tetR operator into a vector, such as a plasmid or a phage, to facilitate its propagation. Cloned operator sequence may then be rendered available for insertion into a promoter of interest, as set forth in Section 5.2., infra.

In a particular, nonlimiting embodiment of the invention, tetR operator sequence may be cloned as follows: Four oligonucleotides, which when annealed produce the two 19 bp OP1 and OP2 palindromic sequences of the tetR operator may be synthesized; the sequences of said oligonucleotides are as follows:

X-1 (SEQ ID NO:12). 5'ACTCTATCATTGATAGAGT3'

X-2 (SEQ ID NO:13). 5'ACTCTATCAATGATAGAGT3'

X-3 (SEQ ID NO:14). 5'TCCCTATCAGTGATAGAGA3'

X-4. 5'TCTCTATCACTGATAGGGA3'

Oligonucleotides X-1 and X-2 are complementary and, when annealed, form the OP1 operator. Similarly, oligonucleotides X-3 and X-4, when annealed, produce the OP2 operator site. The OP1 oligonucleotides may then be directly cloned into the EcoRV site of the Bluescript (Stratagene) polylinker to form plasmid X. OP2 oligonucleotides may then be cloned into a Mung bean nuclease blunted ClaI site of plasmid X to form plasmid Y. The resulting tetR operator may then be propagated and then excised from plasmid Y as an EcoRI, AccI fragment which may be end-filled with T4 polymerase and gel purified.

It is preferable that the separation between OP1 and OP2 is about 10–11 bp.

Analogous methods may be used to insert the tetR operator site into other suitable vectors.

5.2. Modified Promoters Containing the tetR Operator

According to the invention, the tetR operator may be inserted into a suitable animal promoter so as to render that promoter subject to repression by tetR repressor protein. Any animal promoter maybe used; strategies for promoter selection are set forth in Section 5.3., infra.

In preferred embodiments of the invention, the tetR operator sequence is positioned 3' to the TATA-box sequence. A nonlimiting list of promoters which may be used according to the invention is set forth in FIG. 6, together with the proximal portion of the promoter in the vicinity of the TATA-box, which is underlined.

In a specific, nonlimiting embodiment of the invention, the tetR operator site may be inserted into the NheI site of the PEPCK promoter (Wynshaw-Boris et al., 1984, J. Biol. Chem. 259:12161–12169). A diagram of the PEPCK promoter containing the tetR operator sequence of the NheI site is presented in FIG. 2. For insertion of the operator sequence, the PEPCK promoter may be cut with NheI and end-filled with T4 polymerase; tetR opera tor, prepared as set forth in Section 5.1., suara, may then be blunt-ligated into place.

5.3. Utility of the Invention

5.3.1. STRATEGY

The strategy of the invention is to prepare a non-human transgenic animal that comprises two transgenes. The first transgene, termed "A," is a gene of interest, the expression of which is desirably controlled. Virtually any gene of interest may be. used, including, but not limited to, growth hormone, hemoglobin, low density lipoprotein receptor, insulin, genes set forth in Table I, etc.

TABLE 1

Other Genes Of Interest

| Gene | Disease/Affect |
|---|---|
| ADA Adenosine deaminase | Immuno-deficiency |
| TNF Tumor necrosis factor | Anti-cancer |
| IL-2 Interleukin-2 | Anti-cancer |
| LDL low density | hypercholesterolemia |
| Factor IX | hemophelia |
| Factor VIII | hemophelia |
| β-glucosidase | Gauchers disease |
| CFTR Cystic fibrosis transmembrane regulator | Cystic fibrosis |
| HPRT Hypoxanthine-quanine phosphoribosyltransferase | Lesch-Nyhan syndrome |
| UDP-glucuronyl transferase | Crigler-Najjar syndrome |
| Growth Hormone receptor | Growth |
| Insulin-like growth factor | Growth |
| Growth hormone releasing factor | Growth |

The expression of gene "A" is under the transcriptional control of promoter "B". Promoter B comprises a tetR operator sequence, as discussed supra. Promoter B desirably defines the time and tissue window in which the transgene may be induced; for example, promoter A may be a tissue specific promoter such as the PEPCK promoter (which is expressed selectively in liver and becomes active shortly prior to birth). The second transgene encodes the tetR repressor, the sequence of which is set forth in FIG. 5.

Analysis of the Tn10 tetR coding sequence indicates that the codon usage for this gene is poorly suited for expression in mammalian cells (FIG. 15). To optimize tetR expression in mammalian cells a new tetR repressor gene was designed (See, Section 7, infra), which may be utilized in alternative embodiments of the invention. The synthetic tetR gene (syn-tetR) is designed to encode exactly the same protein product as the bacterial Tn10 tetR gene but optimizes codon usage for mammalian cells. The percentage of G and C bases has been significantly improved, while the frequency of CpG base pairs has been minimized. A CpG base pair is frequently the site for DNA methylation which can negatively affect the expression of a gene. In addition, the syn-tetR gene is devoid of any splice signals, decreasing the likelihood of aberrant splicing of the RNA which may result in production of a non-functional message. The sequence of the synthetic tetR gene is depicted in FIG. 16. Plasmids comprising these sequences may be constructed using plasmids pLT-1, pLT-2, pLT-3 and pLT-5 (deposited with the American Type, Culture Collection (ATCC) and assigned accession numbers 69396, 69397, 69398, and 69399, as described in Section 7, infra.

In further embodiments, the present invention provides for additional synthetic tetR genes from which one or more splice sites have been deleted or for which codon usage has been further optimized.

The present invention covers synthetic tetR genes having the sequence set forth in FIG. 16 and for functionally equivalent variants of that sequence.

In specific, non-limiting embodiments of the invention, a nuclear localization signal may be added to a natural or synthetic tetR gene to facilitate its expression (See, Section 7, infra).

Expression of tetR is controlled by promoter "C". While it is preferable that promoter C be the same as promoter B except that promoter C does not contain a tetR operator sequence, any promoter which provides expression of tetR so as to repress expression of gene "A" during the period when it is desirable to repress expression of "A" may be used.

For example, and not by way of limitation, a transgenic animal may be produced which carries a first transgene which is bovine growth hormone under the control of a PEPCK promoter modified to contain a tetR operator sequence at the NheI site and a second transgene which is tetR repressor protein under the control of an unmodified PEPCK promoter; see Section 6, infra. The pPCK_NbGH construct has been deposited with the ATCC and assigned accession number 69400.

5.3.2. TRANSGENIC ANIMALS OF THE INVENTION

The binary repressor system of the invention may be used to control gene expression in any non-human transgenic animal, including, but not limited to, transgenic mice, pigs, goats, cows, rabbits, sheep, etc. The present invention provides for such non-human transgenic animals carring as transgenes nucleic acid constructs described herein, including natural or synthetic tetR repressor proteins and operator sequences.

Transgenes may be introduced by microinjection, transfection, transduction, electroporation, cell gun, embryonic stem cell fusion, or any other method known in the art. The transgenes of the invention may be co-introduced into a single animal or may be introduced into two individual animals that are subsequently mated to produce doubly transgenic offspring.

For example, for the production of transgenic mice, the following general protocol may be used. Male and female mice are mated at midnight. Twelve hours later, the female may be sacrificed and the fertilized eggs may be removed from the uterine tubes. Foreign DNA may then be microinjected (100–1000 molecules per egg) into a pronucleus. Shortly thereafter, fusion of the pronuclei (a pronucleus or the male pronucleus) occurs, and, in some cases, foreign DNA inserts into (usually) one chromosome of the fertilized egg or zygote. The zygote may then be implanted into a pseudo-pregnant female mouse (previously mated with a vasectomized male) where the embryo develops for the full gestation period of 20–21 days. The surrogate mother then delivers the mice and by four weeks transgenic pups may be weaned from the mother.

According to another embodiment of the invention, a transgenic pig may be produced, briefly, as follows. Estrus may be synchronized in sexually mature gilts (>7 months of age) by feeding an orally active progestogen (e.g. allyl trenbolone, AT: 15 mg/gilt/day) for 12 to 14 days. On the last day of AT feeding all gilts may be given an intramuscular injection of prostaglandin $F_{2\alpha}$ (Lutalyse: 10 mg/injection) at 0800 and 1600 hours. Twenty-four hours after the last day of AT consumption all donor gilts may be administered a single intramuscular injection of pregnant mare serum gonadotrophin (1500 U). Human chorionic gonadotrophin (750 IU) may be administered to all donors at 80 hours after pregnant mare serum gonadotrophin.

Following AT withdrawal, donor and recipient gilts may be checked twice daily for signs of estrus using a mature boar. Donors which exhibited estrus within 36 hours following human chorionic gonadotrophin administration may be bred at 12 and 24 hours after the onset of estrus using artificial and natural (respectively) insemination.

Between 59 and 66 hours after the administration of HCG one- and two-cell ova may be surgically recovered from bred donors using the following procedure. General anesthesia may be induced by administering 0.5 mg of acepromazine/kg of bodyweight and 1.3 mg of ketamine/kg via a peripheral ear vein. Following anesthetization, the reproductive tract may be exteriorized following a mid-ventral laparotomy. A drawn glass cannula (O.D. 5 mm, length 8 cm) may be inserted into the ostium of the oviduct and anchored to the infundibulum using a single silk (2-0) suture. Ova may then be flushed in retrograde fashion by inserting a 20 g needle into the lumen of the oviduct 2 cm anterior to the uterotubal junction. Sterile Dulbecco's phosphate buffered saline (PBS) supplemented with 0.4% bovine serum albumin (BSA) may be infused into the oviduct and flushed toward the glass cannula. The medium may be collected into sterile 17×100 mm polystyrene tubes. Flushings may be transferred to 10×60 mm petri dishes and searched at a lower power (50×) using a Wild M3 stereomicroscope. All one- and two-cell ova may be washed twice in Brinster's Modified Ova Culture -3 medium (BMOC -3) supplemented with 1.5% BSA and transferred to 50 $\mu$l drops of BMOC-3 medium under oil. Ova may be stored at 38° C. under a 90% $N_z$, 5% $O_z$. 5% $Co_2$ atmosphere until microinjection is performed. One and two-cell ova may be placed in an Eppendorf tube (15 ova per tube) containing 1 ml HEPES medium supplemented wit 1.5% BSA and centrifuged for 6 minutes at 14,000 g in order to visualize pronuclei in one-cell and nuclei in two-cell ova. Ova may then be transferred to a 5–10 $\mu$l drop of HEPES medium under oil on a depression slide. Microinjection may be performed using a Laborlux microscope with Nomarski optics and two Leitz micromanipulators. 10–1700 molecules of construct DNA (linearized at a concentration of about 1 ng/$\mu$l of Tris-EDTA buffer) may be injected into one pronucleus in one-cell ova or both nuclei in two-cell ova. Microinjected ova may be returned to microdrops of BMOC-3 medium under oil and maintained at 38° C. under a 90% $N_2$, 5% $CO_2$, 5% $O_2$ atmosphere prior to their transfer to suitable recipients. Ova may preferably be transferred within 10 hours of recovery. Only recipients which exhibit estrus on the same day or 24 hours later than the donors may preferably be utilized for embryo transfer. Recipients may be anesthetized as described supra. Following exteriorization of one oviduct, at least 30 injected one- and/or two-cell ova and 4–6 control ova may be transferred in the following manner. The tubing from a 21 g×¾ butterfly infusion set may be connected to a 1 cc syringe. The ova and one to two mls of BMOC-3 medium may be aspirated into the tubing. The tubing may then be fed through the ostium of the oviduct until the tip reaches the lower third or isthmus of the oviduct. The ova may be subsequently expelled as the tubing is slowly withdrawn. The exposed portion of the reproductive tract may be bathed in a sterile 10% glycerol 0.9% saline solution and returned to the body cavity. The connective tissue encompassing the linea alba, the fat, and the skin may be sutured as three separate layers. An uninterrupted Halstead stitch may be used to close the linea alba. The fat and skin may be closed using a simple continuous and mattress stitch, respectively. A topical antibacterial agent (e.g. Furazolidone) may then be administered to the incision area. Recipients may be penned in groups of about four and fed 1.8 kg of a standard 16% crude protein corn-soybean pelleted ration. Beginning on day 18 (day 0=onset of estrus), all recipients may be checked daily for signs of estrus using a mature boar. On day 35, pregnancy detection may be performed using ultrasound. On day 107 of gestation recipients may be transferred to the farrowing suite. In order to ensure attendance at farrowing time, farrowing may be induced by the administration of prostaglandin $F_{2a}$ (10 mg/injection) at 0800 and 1400 hours on day 112 of gestation. In all cases, recipients may be expected to farrow with 34 hours following PGF 2a administration.

As used herein, the term "transgenic animal" refers to animals that carry a transgene in at least some of their somatic cells, and preferably in at least some of their germ cells.

5.3.3. INDUCTION

Induction of expression of the gene of interest in transgenic animals of the invention may be achieved by administering, to the animal, a compound that binds to tetR so that tetR repressor function is inhibited. Examples of such compounds include tetracycline and tetracycline-like compounds, including, but not limited to, apicycline, chlortetracycline, clomocycline, demeclocycline, guamecycline, lymecycline, meclocycline, methacycline, minocycline, oxytetracycline, penimepicycline, pipacycline, rolitetracycline, sancycline, and senociclin.

Administration of the inducer can be through direct injection, water, feed, aerosol, or topical application. The choice of method will depend on the promoters used and the specific application of the transgenic animals. For example, injection, water and feed would provide inducer to all of the animals tissues. In our case, administration through water or feed would be the preferred method to control growth hormone expression in transgenic pigs. Aerosol spray could be used to attain high antibiotic concentrations in the lung. This may be appropriate for example in a cystic fibrosis or emphysema model. Topical application to the skin is also possible and could be used in models of acne, hair loss, wound healing or viral infection.

Induction of the gene of interest is accomplished by administering an effective amount of inducer, as described above. An effective amount of inducer may be construed to mean that amount which increases expression of the gene of interest by at least about 50 percent. As the $LD_{50}$ for tetracycline HCl in rats is about 6643 mg/kg and the therapeutic dose is between about 25–50 mg/kg, an effective dose of tetracycline, as inducer, is between about 5–50 mg/kg and preferably between about 5–15 mg/kg.

6. EXAMPLE: TETRACYCLINE REPRESSOR-MEDIATED BINARY REGULATION SYSTEM FOR CONTROL OF BOVINE GROWTH HORMONE EXPRESSION IN TRANSGENIC MICE 6.1. Materials and Methods 6.1.1. CONSTRUCTION OF PLASMIDS Plasmid p∂∂7 contains a functional tetR operator site cloned within a Bluescript (Stratagene) polylinker. This plasmid is useful for propagating the operator sequence, and as a source of operator sites for insertion into the PEPCK promoter or any other promoter element. The p∂∂7 plasmid was made as follows. Four oligonucleotides, which when annealed produce the two 19 bp OP1 and OP2 palindromic sequences of the tetR operator were synthesized. The sequences of each oligonucleotide is listed below.

X-1.5' ACTCTATCATTGATAGAGT 3' (SEQ ID NO:12)
X-2.5' ACTCTATCAATGATAGAGT 3' (SEQ ID NO:13)
X-3.5' TCCCTATCAGTGATAGAGA 3' (SEQ ID NO:14)
X-4.5' TCTCTATCACTGATAGGGA 3' (SEQ ID NO:15)

Oligonucleotides X-1 and X-2 are complementary and when annealed form the OP1 operator. Similarly oligonucleotides X-3 and X-4 produce the OP2 operator site. The OP1 oligonucleotides were directly cloned into the EcoRV site of the Bluescript polylinker. The resulting plasmid pSOPI was sequenced to verify the integrity of the insert. OP2 oligonucleotides were subsequently cloned into a Mung bean nuclease blunted ClaI site of pSOPI to produce p∂∂7. Due to a cloning artifact produced by the Mung bean nuclease, the operator in p∂∂7 consists of the two 19 bp OP1 and OP2 sequences separated by linker of only 10 base pairs. This difference does not effect tetR binding. The sequence of the p∂∂7 operator site is shown in FIG. 1B. The 55 base pair tetR operator was excised from p∂∂7 as an EcoRl, AccI fragment, end filled with T4 polymerase, and gel purified. This fragment was subsequently used to produce the modified PEPCK promoters Pck_N and Pck_A.

Plasmids Pck_A and Pck_N were produced by inserting the 55 bp tetR operator into the unique AccI and NheI sites (respectively) of the PEPCK promoter (pPCK_NbGH has been deposited with ATTC and assigned accession No: 69400). For both plasmids the promoter was cut with the appropriate restriction enzyme, end filled with T4 polymerase and the tetR operator blunt ligated into place. A third modified PEPCK promoter, Pck_T was produced in which the OP1 and OP2 operator sequences were positioned to flank the PEPCK TATA-box element. To produce Pck_T a new oligonucleotide (5'ACTCTATCATTGATAGAGTTACTAT TTAAATCCCTATCAGTGATAGAGA3')(SEQ ID NO:13)) was produced. This oligonucleotide was kinased with T4 polynucleotide kinase and annealed to kinased X-2 and X-4 which are complementary to the first and last 19 bp. The complete double stranded 49 bp operator was produced by filling in the 11 bp linker region, which includes the PEPCK TATA-box element, with Klenow. The final product was then blunt cloned into an AccI, NheI cut PEPCK promoter. All three modified promoters were sequenced to verify the inserts. FIG. 2 depicts the structure of these promoters.

6.1.2. REPRESSOR CONSTRUCT

Plasmid pBI501 contains a 701 bp HincII fragment from E. coli Tn10, cloned into the HincII site of pUC8. The HincII insert contains the entire tetR coding sequence along with 21 bp of 5' and 55 bp of 3' untranslated DNA. This insert was excised from the parent plasmid and subcloned into a plasmid with a more suitable polylinker to produce pSTET7.

To this plasmid a 870 bp XhoI, BamHI fragment derived from PMSG (Pharmacia), containing the SV40 small-T intron and polyadenylation signal sequences was inserted at the HindII site 3' of the tetR coding region to produce pSTetRSv. Finally an unmodified 610 bp PEPCK promoter was inserted at the EcoRl site of pSTETRSv to produce pPck_tetRSv. The PEPCK promoter is identical to the promoter used to produce pPck_A, pPck_N, and pPck_T except that it does not contain a tetR operator site. This PEPCK promoter has been previously used in transgenic animals and is known to target gene expression specifically to the liver.

6.1.3. GROWTH HORMONE GENES

Plasmid pGH-SAF107 contains a 2.2 kb BamHI, EcoRI genomic fragment of the bovine growth hormone (bGH) gene, blunt ligated into an EcoRV site. To this vector each of the modified PEPCK promoters was added by blunt ligating the promoter into the BamHl site of pGH-SAF107. The structure of the resulting plasmids is depicted in FIG. 3. Plasmid pPCK_NbGH was deposited with the ATCC and assigned accession number 69400. For production of transgenic animals, each of the PEPCK-bGH genes was excised from the vector using Xhol and Sacl, gel fractionated and purified using an Elutip column.

6.1.4. TRANSGENIC MICE

Transgenic mice were made which contain both the Pck_tetRSv gene and one of the modified PEPCK promoters controlling bGH. Table 2 lists the number of eggs injected, offspring produced and number of transgenics derived for each construct.

TAELE 2

| Construct | Eggs injected | Eggs transferred | Live Born | Transgenic |
| --- | --- | --- | --- | --- |
| Pck_AbGH + Pck_tetRSv (251) | 233 | 194 | 40 | 14 (0.35) |
| Pck_NbGH + Pck_tetRSv (252) | 268 | 208 | 30 | 9 (0.3) |
| Pck_TbGH + Pck_tetRSv (261) | 227 | 197 | 25 | 5 (0.2) |

6.2. Results and Discussion

Once the transgenic founder animals were identified, they were weighed each week. Table 3 lists the mean weights of each group of transgenic animal at 11 weeks of age.

TABLE 3

| Construct | Sex | Weight |
| --- | --- | --- |
| Pck_AbGH + Pck_tetRSv (9) | male | 36.122 (12.251) |
| Pck_AbGH + Pck_tetRSv (4) | female | 29.125 (7.861) |
| Pck_NbGH + Pck_tetRsv (5) | male | 34.840 (14.745) |
| Pck_NbGH + Pck_tetRSv (4) | female | 28.125 (10.958) |
| Pck_TbGH + Pck_tetRSv (3) | male | 36.267 (11.402) |
| Pck_TbGH + Pck_tetRSv (2) | female | 27.300 (5.798) |
| NON-TRANSGENIC (6) | male | 29.583 (2.395) |
| NON-TRANSGENIC (6) | female | 23.117 (1.863) |

As expected for each co-injection, large animals, obviously expressing elevated levels of bGH, were observed as were animals of normal stature.

At 10 weeks of age, a sampling of transgenic female founders containing the A+T and N+T were tested for induction of bGH in the serum using a radio-immune assay, after a single IP injection of 60 mg/kg tetracycline-HCl. The purpose of this experiment was simply to determine which if either of these two modified promoters was responsive to repression by tetR. The results are summarized in Table 4.

TABLE 4

| Construct | Animal | Weight | Basal | 12 hours | 36 hours |
| --- | --- | --- | --- | --- | --- |
| 249 | 2-5 female | 21.1 | 0.00 | 0.00 | 0.00 |
| 250 | 6-6 female | 42.9 | 4.6 ± 0.033 | 3.4 ± 0.062 | 4.9 ± 0.072 |
| 251 | 6-6 female | 19.3 | 0.00 | 0.00 | 0.00 |
| 251 | 10-5 female | 25.1 | 0.20 ± 0.008 | 0.19 ± 0.001 | 0.21 ± 0.038 |
| 252 | 5-2 female | 38.7 | 0.59 ± 0.107 | 0.64 ± 0.044 | 1.12 ± 0.207 |
| 252 | 5-3 female | 20.0 | 0.00 | 0.00 | 0.00 |
| 252 | 10-2 | 19.2 | 0.00 | 0.00 | 0.00 |

No induction of bGH was observed in animals that lack the Pck_tetRSV gene (construct 250) or in animals with both the Pck_AbGH+Pck-tetRSv genes (construct 251). An approximate two fold increase in serum bGH levels was however detected in the 5-2 female which contains the Pck-NbGH+Pck_tetRSV genes. The remainder of the animals had undetectable levels of bGH expression, due in part to the relatively low sensitivity of this assay. For example the 10-2 female (construct 252) shows no detectable bGH in the serum, but subsequent expieriments on her offspring indicate that this line of animals does express bGH mRNA in a tetracycline dependent manner. This initial data, suggested that the Pck_N promoter was being regulated by tetR at least to a limited extent.

To further characterize the mice, improve the sensitivity of the assay and to test the responsiveness of the Pck_T promoter, offspring of founder mice from each co-injection were produced. The transgenic progeny were then raised in the presence or absence of tetracycline medicated water (500 $\mu$g/ml) for 4 weeks, prior to analysis of bGH mRNA expression levels in the liver, the predominant site of PEPCK expression. Northern blot hybridization analysis of these animals (FIG. 7) demonstrated again, that animals with the Pck_NbGH gene were responsive to repression by tetR and that the other two modified promoters exhibited no signs of tetR dependent regulation.

We attempted to breed all of the remaining founders containing the Pck-NgGH+Pck_tetRSv genes to analyze their offspring in a similar manner (FIG. 8). Of the 5 founders which produced offspring, 2 did not express bGH under any conditions, and from the remaining 3 one segregated two different integration sites allowing us to establish a total of 4 lines. All 4 lines exhibited tetracycline dependent bGH expression as assayed by Northern blot hybridization. The efficiency of tetR repression appeared to be inversely correlated with the level of expression. For example 9-5 animals have the highest level of bGH expression, show an obvious increase in body size, and exhibit only marginal tetR repression. In contrast 9-4Lc and 10-2 animals exhibit lower levels of tetracycline induced bGH expression, are of normal stature and appear to be efficiently regulated by tetR.

An S1 nuclease protection assay was performed to identify the start site of transcription of bGH mRNA. As shown in FIG. 4, there was only one start site identified regardless of the presence or absence of tetR repressor binding. This start site was located approximately 20 bp downstream from the TATA-box. At this location, the message is initiating within the $\partial\partial 7$ operator sequence, just 3 or 4 base pairs 5' of the first tetR binding site.

7. EXAMPLE: OPTIMIZATION OF tetR CODING SEQUENCE

The use of the wild type Tn10 tetR gene in conjunction with the 252 construct indicates that the TetR system can function in transgenic animals and that in some cases, for instance in the 10-2 transgenic animals, the level of regulation can be very high (FIGS. 9A and 9B). However, in other instances the efficiency of repression is not always complete, leading to a significant basal level of bGH expression. This failure to repress may be due to low level expression of tetR. To optimize the expression of tetR repressor, a synthetic tetR gene was generated which was devoid of splice signals and had optimized codon usage for mammalian cells.

7.1 Materials and Methods

7.1.1. TISSUE SPECIFICITY AND TETRACYCLINE INTRODUCTION OF bGH IN LINE 10-2

For all Northern blots 10 μg of whole RNA was electrophoreses through a 1% agarose gel containing 3% formaldehyde using standard techniques. To detect bGH mRNA a random primed, radioactive bGH cDNA probe was used. All conditions for hybridization and washing of filters were done in accordance with standard techniques of molecular biology.

7.1.2. EXPRESSION AND ALTERNATIVE PROCESSING OF THE tetR TRANSGENE

A RNase protection probe which extended from the NruI site of tetR 3' to the end of the gene was used. This probe includes only tetR coding sequences and should give a fully protected fragment of approximately 400 base pair. When hybridized to 150 μg of liver RNA (500,000 cpm of probe in a 30 μl hybridization consisting of 80% formamide, 40 mM PIPES pH 6.4, 400 mM NaOAc, and 1 mM EDTA), and digested with RNase one (Promega) for 30 minutes at 370 as recommended by the manufacturer, a protected fragment of approximately 221–260 base pairs is observed, far smaller than predicted.

7.1.3. 5' STRUCTURE OF tetR mRNA

Liver RNA was treated with reverse transcriptase and amplified by PCR using the manufacturers recommended conditions (Pharmacia). The RNA was amplified using two different pairs of primers. The first primer pair (TZ-1 and TZ-4) should produce a 619 base pair product. The second primer pair (TZ-3 and TZ-4) should produce a 498 base pair product. The sequence of the primers are:

TZ-1: 5'CCGCATATGATCAATTCAAGGC-CGAATAAG3'

TZ-3: 5'CTTTAGCGACTTGATGCTCTTGATCT-TCCA3'

TZ-4: 5'AATTCGCCAGCCATGCCAAAAAAGAA-GAGG3'

The TZ-4 primer is common to both primer pairs and is the 5' primer which encompasses the start codon of the tetR mRNA. Primer TZ-1 and TZ-3 are two different 3' primers both of which are in the tetR coding region. When amplified, these primer pairs produce smaller than expected products (approx. 215 bp vs. 619 bp for TZ-4 and TZ-1, and approx. 94 bp vs. 498 bp for TZ-4 and TZ-3). The products of this reaction were cloned and sequenced. The sequence revealed the presence of an unexpected intron which spanned from near the Xbal site at the start of tetR to a splice acceptor just 8 base pairs 5' of the TZ-3 primer.

7.1.4. 345 REPRESSOR CONSTRUCT

In an embodiment of the invention, any nuclear localization signal may be added to a natural or synthetic tetR gene to facilitate its expression. For example, complementary oligonucleotides which encode a nuclear localization signal sequence were synthesized (Oligos etc.) and added in frame to the tetR coding sequences of pSTETR107 at the EcoR1 and Xbal restriction sites to produce pNTETR. Oligonucleotide sequences are: (GB1) (SEQ ID NO:24) 5'AATTCGC-CAGCCATGCCAAAAAAGAAGAGGAAGGTAT3' and (GB2) (SEQ ID NO:24) 5'CTAGATACCTTCCTCT-TCTTTTTTGGCATGGCTGGC3'. When annealed these oligonucleotides have a 5' EcoR1 and 3' Xbal compatible overhangs. These oligonucleotides fuse the amino acid sequence Met Pro Lys Lys Lys Arg, Lys Val,to the third amino acid (Arg) of wild type tetR.

Two complementary 51 base pair oligonucleotides which start the 5' cap site of bGH and extend to the first exon were synthesized (Oligos etc.). Sequence for the oligonucleotides are (5b-1) (SEQ ID NO:25): 5'GATCCCAGGACCCAGT-TCACCAGACGACTCAGGGTCCTGTGGACAGCT CAG3' and (5b-2) (SEQ ID NO:26): 5'AATTCTGAGCT-GTCCACAGGACCCTGAGTCGTCTGGT-GAACTGGGTCC TGG3'. When annealed these oligonucleotides have 5' BamH1 and 3'EcoR1 compatible overhands. The oligonucleotides for the 5'leader sequence of bGH were cloned into a BamH1, EcoR1 cut plasmid to produce p5' GH.

The nuclear localization modified tetR coding sequence was isolated by gel purification after restriction digestion of pNTETR using EcoR1 and Hind III. This fragment was then inserted into p5'GH at the EcoR1 and Hind III sites to product p5'GHTR.

To add the remainder of the bGH genomic sequence an intermediate modification of p5'GHTR was first made. This modification consisted of adding a Hind III—Pst1 linker to the Hind III site of p5'GHTR to product pGTO. The sequence of the oligonucleotides which comprise this linker are: (CC-1) (SEQ ID NO:27) 5'AGCTTCTGCAG3' and (CC-2) (SEQ ID NO:28) 5'AGCTCTGCAGA3'. The remaining bGH genomic sequences were added in two steps. First the Pst1 Sac2 fragment that begins in the first exon of bGH and ends in the third intron was excised from pSGH107. Similarly, the insert of pGTO which contains the 5' untranslated leader of bGH and the nuclear localization modified tetR was excised using BamH1 and Pst1. These two gel purified fragments was then cloned into a BamH1 Sac2 cut vector to produce pGTG. Finally, the remainder of the bGH gene from the Sac2 site in the third intron to the end of the gene, was added to pGTG by cutting pGTG with Sac2 and adding the Sac2 fragment from pSGH106 to produce pNTETR-GH.

Plasmid pNTETR-GH was digested with BamH1 to excise the NTETR-GH gene. The fragment was cloned into the BamH1 site of pPCK 305 to produce the final plasmid pPCK-GHNTET. To produce transgenic mice, the PEPCK-GHTET gene was excised from the plasmid using Sa11 and Sac1. This fragment was gel purified and coinjected with the PCK-NbGH gene previously described to generate transgenic mice.

7.1.5. SYNTHETIC tetR COMPONENT SEQUENCES

The components of the synthetic tetR gene were synthesized by Midland Laboratories as four overlapping double stranded DNA cassettes. The sequence of these cassettes are shown in FIG. 15. Each cassette was blunt cloned into the Hinc2 site of pUC19 and sequenced to verify authenticity. The resulting plasmids PLT1, pLT2, pLT3 and pLT5 can be used as the source material to assemble the entire synthetic tetR coding sequence since each contains an overlapping unique restriction site (bold face) through which they can be joined (pLT-1, pLT-2, pLT-3 and pLT-5 have been deposited with ATCC and have been assigned accession numbers 69396, 69397, 69398, and 69399 respectively). There are many possible ways by which these cassettes can be joined. By way of an example, the inserts of plasmid pLT1 and pLT2 can be excised using EcoR1 and Nsi1. The inserts can then be combined by cloning these two fragments into an EcoR1 vector. This procedure will assemble the 5' half of the gene, using the overlapping NsiI restriction site to join the pieces. Similarly, the 3' half of the gene can be assembled from pLT3 and pLT5 by cutting with EcoR1 and Sph1 (pLT3) and SphI and Hind III (pLT5) to release the inserts. These inserts can then be joined at the overlapping Sph1 site by cloning the fragments into an EcoR1, Hind III cut vector. Finally, the entire coding region can be put together using the overlapping restriction site ApaL1. This would result in a vector with the synthetic tetR coding sequence, as depicted in FIG. 16, cloned into a plasmid as an EcoR1 Hind III fragment.

7.1.6. COMPOSITIONAL ANALYSIS OF WILD TYPE Tn10 tetR GENE

The Tn10 tetR coding sequence was analyzed on a desktop computer using Mac Vector software. FIG. 14 shows a diagram of the tetR coding region with all of the plus strand splice doner (D) and splice acceptor (A) signal sequences indicated. For reference the location of the XbaI restriction is also indicated. The first graph depicts the percentage of G and O bases in the coding region of tetR. There are several domains of very low GC content. The bottom graph is an analysis of codon bias. The dark line is a comparison of the tetR codon usage to a mouse codon bias table. Values much lower than 1.0 are indicative of sequences which may translate poorly. For reference, a comparison of tetR to a Tobacco codon bias table is included (light line). In transgenic tobacco, the tetR regulation system functions very efficiently, suggesting that for this gene, codon bias may be an important factor for efficient expression.

7.1.7. COMPOSITIONAL ANALYSIS OF SYNTHETIC tetR

FIG. 17 depicts the structure of the synthetic tetR gene, now devoid of splice donor signal sequences, with only a single splice acceptor signal remaining (A). This is not the splice acceptor which was active in the 345 construct. The percentage of G and C bases has been significantly improved, while the frequency of CpG base pairs has been kept to a minimum. A CpG base pair is frequently the site for DNA methylation, which can negatively effect the expression of a gene. The codon bias of the synthetic tetR gene is vastly improved. The graph depicts the results when the synthetic tetR coding sequence is compared to the same mouse codon bias table used previously.

7.2 Results
7.2.1. EXPRESSION OF tetR IN CONSTRUCT 345 OFFSPRING

To improve tetR expression a new repressor construct was produced. The construct, referred to as Construct 345 is depicted in FIG. 10. In the 345 construct the coding region of tetR is augmented with a nuclear localization signal sequence to increase the nuclear concentration of repressor. The tetR coding region was inserted into the first exon of the bGH gene. The bGH gene then acts as a genomic carrier, providing multiple introns, which may improve expression, and a strong polyadenylation signal, which may improve the processing and stability of the message.

The new repressor was coinjected with the bGH gene from construct 252. The resulting transgenic animals contain the new repressor, and a PEPCK regulated bGH gene with the tetR operators located just 3' of the PEPCK TATA-box element. Offspring of these animals were screened for bGH induction (FIG. 11). Of the lines tested only one, line 14, showed tetracycline dependent regulation of bGH, and in this one case there was still a significant base level of bGH expression. Northern analysis, performed to determine the levels of tetR mRNA expressed in the transgenic mice, indicated that the tetR gene was still not expressed at a high level.

To detect tetR mRNA with higher sensitivity the tetR mRNA was analyzed using RNase protection. This technique revealed that the mRNA was shorter then expected (FIG. 12). Subsequent analysis using reverse ranscriptase-PCR with primers that amplify the entire coding region of tetR confirmed that the mRNA was significantly shorter then expected (FIG. 13). Sequence analysis of these RT-PCR products indicated that an unexpected splicing event had occurred. This splicing process occurred between a splice donor signal in the 5' end of the tetR coding region and a splice acceptor approximately 400 bp 3' of the start codon. The resulting mRNA is therefore deleted of the tetR DNA binding domain and about two third of the entire coding region. This RNA could not possibly make a functional repressor.

7.2.2. OPTIMIZATION OF tetR CONSTRUCT

A more detailed analysis of the tetR coding sequence indicated that the codons used in this gene are poorly suited for expression in mammalian cells (FIG. 14). Therefore, it appears that the inefficiency of the tetR system is the result of two processes: (i) aberrant splicing of the RNA to produce a nonfunctional message; and (ii) inefficient translation which can lead to rapid mRNA turnover.

To circumvent the problems of internal splicing and potential problems due to codon bias and G–C content, a synthetic tetR gene was designed. The components of the synthetic tetR gene were synthesized as four overlapping double stranded cassettes. Each cassette was cloned in puc19. The resulting plasmids designated pLT-1, pLT-2, pLT-3 and pLT-5, as depicted in FIG. 15, have been deposited with ATCC and assigned accession numbers 69396, 69397, 69398, and 69399, respectively. The synthetic tetR (syn-tetR) has been designed to encode exactly the same protein product, but is devoid of splice signals and has greatly improved codon usage for mammalian cells. The sequence of the of the syn-tetR is indicated in FIG. 16. The predicted analysis for splicing signals, G+C content, and codon usage are depicted in FIG. 17.

8. DEPOSIT OF MICROORGANISMS

The following microorganisms have been deposited with the American Type Culture Collection, (ATCC), Rockville, Md. and have been assigned the following accession numbers:

| Microorganism | Date of Deposit | Accession No. |
| --- | --- | --- |
| pLT-1 | August 25, 1993 | 69396 |
| pLT-2 | August 25, 1993 | 69397 |
| pLT-3 | August 25, 1993 | 69398 |
| pLT-5 | August 25, 1993 | 69399 |
| pPCK_NbGH | August 25, 1993 | 69400 |

The present invention is not to be limited in scope by the microorganisms deposited since the deposited embodiments are intended as illustrations of single aspects of the invention and any microorganisms which are functionally equivalent are within the scope of the invention.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

Various publications are cited herein, which are hereby incorporated by reference in their entirety.

```
                           SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
         (A) LENGTH: 59 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:1:

TTGACACTCT ATCATTGATA GAGTTATTTT ACCACTCCCT ATCAGTGATA GAGAAAAGT          59

(2) INFORMATION FOR SEQ ID NO:2:

(i) SEQUENCE CHARACTERISTICS:
         (A) LENGTH: 70 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:2:

GAATTCGATA CTCTATCATT GATAGAGTAT CAAGCTTATC CCTATCAGTG ATAGAGATAC         60

CGTCGACCTC                                                               70

(2) INFORMATION FOR SEQ ID NO:3:

(i) SEQUENCE CHARACTERISTICS:
         (A) LENGTH: 49 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:3:

ACTCTATCAT TGATAGAGTT ACTATTTAAA TCCCTATCAG TGATAGAGA                     49

(2) INFORMATION FOR SEQ ID NO:4:

(i) SEQUENCE CHARACTERISTICS:
         (A) LENGTH: 71 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO:4:
```

-continued

```
GGAATTCGAT ACTCTATCAT TGATAGAGTA TCAAGCTTAT CCCTATCAGT GATAGAGATA        60

CCGTCGACCT C                                                            71
```

(2) INFORMATION FOR SEQ ID NO:5:

(i) SEQUENCE CHARACTERISTICS:
        (A) LENGTH: 624 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 1..624

(xi) SEQUENCE DESCRIPTION: SEQ ID NO:5:

```
ATG TCT AGA TTA GAT AAA AGT AAA GTG ATT AAC AGC GCA TTA GAG CTG         48
Met Ser Arg Leu Asp Lys Ser Lys Val Ile Asn Ser Ala Leu Glu Leu
  1               5                  10                  15

CTT AAT GAG GTC GGA ATC GAA GGT TTA ACA ACC CGT AAA CTC GCC CAG         96
Leu Asn Glu Val Gly Ile Glu Gly Leu Thr Thr Arg Lys Leu Ala Gln
                 20                  25                  30

AAG CTA GGT GTA GAG CAG CCT ACA TTG TAT TGG CAT GTA AAA AAT AAG        144
Lys Leu Gly Val Glu Gln Pro Thr Leu Tyr Trp His Val Lys Asn Lys
             35                  40                  45

CGG GCT TTG CTC GAC GCC TTA GCC ATT GAG ATG TTA GAT AGG CAC CAT        192
Arg Ala Leu Leu Asp Ala Leu Ala Ile Glu Met Leu Asp Arg His His
 50                  55                  60

ACT CAC TTT TGC CCT TTA GAA GGG GAA AGC TGG CAA GAT TTT TTA CGT        240
Thr His Phe Cys Pro Leu Glu Gly Glu Ser Trp Gln Asp Phe Leu Arg
 65                  70                  75                  80

AAT AAC GCT AAA AGT TTT AGA TGT GCT TTA CTA AGT CAT CGC GAT GGA        288
Asn Asn Ala Lys Ser Phe Arg Cys Ala Leu Leu Ser His Arg Asp Gly
                 85                  90                  95

GCA AAA GTA CAT TTA GGT ACA CGG CCT ACA GAA AAA CAG TAT GAA ACT        336
Ala Lys Val His Leu Gly Thr Arg Pro Thr Glu Lys Gln Tyr Glu Thr
            100                 105                 110

CTC GAA AAT CAA TTA GCC TTT TTA TGC CAA CAA GGT TTT TCA CTA GAG        384
Leu Glu Asn Gln Leu Ala Phe Leu Cys Gln Gln Gly Phe Ser Leu Glu
        115                 120                 125

AAT GCA TTA TAT GCA CTC AGC GCT GTG GGG CAT TTT ACT TTA GGT TGC        432
Asn Ala Leu Tyr Ala Leu Ser Ala Val Gly His Phe Thr Leu Gly Cys
    130                 135                 140

GTA TTG GAA GAT CAA GAG CAT CAA GTC GCT AAA GAA GAA AGG GAA ACA        480
Val Leu Glu Asp Gln Glu His Gln Val Ala Lys Glu Glu Arg Glu Thr
145                 150                 155                 160

CCT ACT ACT GAT AGT ATG CCG CCA TTA TTA CGA CAA GCT ATC GAA TTA        528
Pro Thr Thr Asp Ser Met Pro Pro Leu Leu Arg Gln Ala Ile Glu Leu
                165                 170                 175

TTT GAT CAC CAA GGT GCA GAG CCA GCC TTC TTA TTC GGC CTT GAA TTG        576
Phe Asp His Gln Gly Ala Glu Pro Ala Phe Leu Phe Gly Leu Glu Leu
            180                 185                 190

ATC ATA TGC GGA TTA GAA AAA CAA CTT AAA TGT GAA AGT GGG TCT TAA        624
Ile Ile Cys Gly Leu Glu Lys Gln Leu Lys Cys Glu Ser Gly Ser *
        195                 200                 205
```

(2) INFORMATION FOR SEQ ID NO:6:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Arg Leu Asp Lys Ser Lys Val Ile Asn Ser Ala Leu Glu Leu
 1               5                  10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

(2) INFORMATION FOR SEQ ID NO:7:

(i) SEQUENCE CHARACTERISTICS:
        (A) LENGTH: 92 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:7:

```
CGGCCCTATA AAAGCGAAG CGCGCGGCGG GCGGGAGTCG CTGCGTTGCC TTCGCCCCGT    60

GCCCCGCTCC GCGCCGCCTC GCGCCGCCCG CC                                 92
```

(2) INFORMATION FOR SEQ ID NO:8:

(i) SEQUENCE CHARACTERISTICS:
        (A) LENGTH: 61 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:8:

```
AAGAAGTATA TTAGAGCGAG TCTTTCTGCA CACACGATCA CCTTTCCTAT CAACCCCACT    60
A                                                                   61
```

(2) INFORMATION FOR SEQ ID NO:9:

(i) SEQUENCE CHARACTERISTICS:
        (A) LENGTH: 74 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:9:

```
GTATTATGTT TTATGTTACT GTAAAAGATG TAAAGAGAGG CACGTGGTTA AGCTCTCGGG    60

GTGTGGACTC CACC                                                     74
```

(2) INFORMATION FOR SEQ ID NO:10:

(i) SEQUENCE CHARACTERISTICS:
        (A) LENGTH: 73 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:10:

```
CGCCCCAAGC ATAAACCCTG GCGCGCTCGC GGCCCGGCAC TCTTCTGGTC CCCACAGACT    60

CAGAGAGAAC CCA                                                      73
```

(2) INFORMATION FOR SEQ ID NO:11:

(i) SEQUENCE CHARACTERISTICS:
        (A) LENGTH: 74 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:11:

```
TAGGCAGCAG GCATATGGGA TGGGATATAA AGGGGCTGGA GCACTGAGAG CTGTCAGAGA    60

TTTCTCCAAC CCAG                                                     74
```

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:12:

```
ACTCTATCAT TGATAGAGT                                                19
```

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:13:

```
ACTCTATCAA TGATAGAGT                                                19
```

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:14:

```
TCCCTATCAG TGATAGAGA                                              19
```

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:15:

```
TCTCTATCAC TGATAGGGA                                              19
```

(2) INFORMATION FOR SEQ ID NO:16:

(i) SEQUENCE CHARACTERISTICS:
        (A) LENGTH: 189 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:16:

```
GATATCGAAT TCATGAGTAG ATTGGACAAG AGCAAAGTGA TCAATAGTGC TCTGGAGCTG   60
TTGAATGAAG TGGGCATAGA AGGTCTGACT ACCAGAAAGC TGGCCCAGAA GCTGGGAGTG  120
GAGCAGCCAA CATTGTACTG GCATGTGAAG AATAAGAGGG CTCTGCTGGA TGCATTGGCG  180
GTACCAGGC                                                         189
```

(2) INFORMATION FOR SEQ ID NO:17:

(i) SEQUENCE CHARACTERISTICS:
        (A) LENGTH: 169 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:17:

```
GCTCGGTACC TGGATGCATT GGCCATTGAG ATGCTGGACA GACACCATAC ACACTTCTGC   60
CCACTGGAAG GCGAGAGTTG GCAGGACTTC CTGAGGAACA ATGCTAAGAG TTTCAGATGT  120
GCTCTGTTGA GCCACAGAGA CGGTGCTAAA GTGCACCTGG AATTCGAGC              169
```

(2) INFORMATION FOR SEQ ID NO:18:

(i) SEQUENCE CHARACTERISTICS:
        (A) LENGTH: 231 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:18:

```
GCTCGAATTC AAAGTGCACC TGGGTACAAG GCCAACAGAG AAACAGTACG AGACCCTGGA        60

GAACCAGCTG GCATTTCTGT GCCAACAAGG CTTCAGCCTG GAGAATGCAT TGTATGCTCT       120

GAGTGCTGTG GGTCACTTCA CACTGGGTTG TCTCCTGGAG GACCAGGAGC ACCAGGTGGC       180

CAAGGAGGAG AGGGAGACCC CAACCACTGA CAGCATGCCC CGGATCCGAG C                231
```

(2) INFORMATION FOR SEQ ID NO:19:

(i) SEQUENCE CHARACTERISTICS:
        (A) LENGTH: 155 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:19:

```
GCTCGGATCC ACAGCATGCC CCCATTGCTG AGACAGGCCT ATGAGCTGTT TGACCACCAA        60

GGGGCAGAGC CTGCTTTTCT GTTTGGCCTG GAGCTCATCA TCTGTGGTCT GGAGAAGCAG       120

CTGAAGTGTG AGAGTGGCTC CTGAAGCTTG ATATC                                  155
```

(2) INFORMATION FOR SEQ ID NO:20:

(i) SEQUENCE CHARACTERISTICS:
        (A) LENGTH: 647 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:20:

```
GATATCGAAT TCATGAGTAG ATTGGACAAG AGCAAAGTGA TCAATAGTGC TCTGGAGCTG        60

TTGAATGAAG TGGGCATAGA AGGTCTGACT ACCAGAAAGC TGGCCCAGAA GCTGGGAGTG       120

GAGCAGCCAA CATTGTACTG GCATGTGAAG AATAAGAGGG CTCTGCTGGA TGCATTGGCC       180

ATTGAGATGC TGGACAGACA CCATACACAC TTCTGCCCAC TGGAAGGCGA GAGTTGGCAG       240

GACTTCCTGA GGAACAATGC TAAGAGTTTC AGATGTGCTC TGTTGAGCCA CAGAGACGGT       300

GCTAAAGTGC ACCTGGGTAC AAGGCCAACA GAGAAACAGT ACGAGACCCT GGAGAACCAG       360

CTGGCATTTC TGTGCCAACA AGGCTTCAGC CTGGAGAATG CATTGTATGC TCTGAGTGCT       420

GTGGGTCACT TCACACTGGG TTGTGTCCTG GAGGACCAGG AGCACCAGGT GGCCAAGGAG       480

GAGAGGGAGA CCCCAACCAC TGACAGCATG CCCCCATTGC TGAGACAGGC CATAGAGCTG       540

TTTGACCACC AAGGGGCAGA GCCTGCTTTT CTGTTTGGCC TGGAGCTCAT CATCTGTGGT       600

CTGGAGAAGC AGCTGAAGTG TGAGAGTGGC TCCTGAAGCT TGATATC                     647
```

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:21:

```
CCGCATATGA TCAATTCAAG GCCGAATAAG                                         30
```

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:22:

```
CTTTAGCGAC TTGATGCTCT TGATCTTCCA                                    30
```

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:23:

```
AATTCGCCAG CCATGCCAAA AAAGAAGAGG                                    30
```

(2) INFORMATION FOR SEQ ID NO:24:

(i) SEQUENCE CHARACTERISTICS:
        (A) LENGTH: 37 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:24:

```
AATTCGCCAG CCATGCCAAA AAAGAAGAGG AAGGTAT                             37
```

(2) INFORMATION FOR SEQ ID NO:25:

(i) SEQUENCE CHARACTERISTICS:
        (A) LENGTH: 51 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:25:

```
GATCCCAGGA CCCAGTTCAC CAGACGACTC AGGGTCCTGT GGACAGCTCA G             51
```

(2) INFORMATION FOR SEQ ID NO:26:

(i) SEQUENCE CHARACTERISTICS:
        (A) LENGTH: 51 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:26:

```
AATTCTGAGC TGTCCACAGG ACCCTGAGTC GTCTGGTGAA CTGGGTCCTG G             51
```

(2) INFORMATION FOR SEQ ID NO:27:

(i) SEQUENCE CHARACTERISTICS:

(A) LENGTH: 11 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:27:

AGCTTCTGCA G                                                                11

(2) INFORMATION FOR SEQ ID NO:28:

(i) SEQUENCE CHARACTERISTICS:
        (A) LENGTH: 11 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:28:

AGCTCTGCAG A                                                                11

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:29:

CTAGATACCT TCCTCTTCTT TTTTGGCATG GCTGGC                                     36

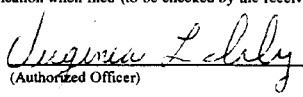

International Application No: PCT/    /

Form PCT/RO/134 (cont.)

American Type Culture Collection

12301 Parklawn Drive
Rockville, MD 10582
US

| Accession No. | Date of Deposit |
|---|---|
| N/A | August 25, 1993 |
| N/A | August 25, 1993 |
| N/A | August 25, 1993 |
| N/A | August 25, 1993 |

What is claimed is:

1. A purified and isolated nucleic acid molecule comprising an optimized tetracycline repressor (tetR) gene as depicted in FIG. 16 (SEQ ID NO: 20).

2. A purified and isolated nucleic acid molecule comprising an optimized tetR gene wherein the tetR gene is devoid of any splice signals and is modified to optimize codon usage for mammalian cells and to increase the percentage of G and C bases while maintaining a low frequency of CpG base pairs.

3. An isolated mammalian host cell which contains and expresses the nucleic acid molecule of claim 2.

4. An isolated mammalian host cell which contains and expresses an optimized tetR gene as depicted in FIG. 16 (SEQ ID NO: 20).

5. A method for expressing the tetR gene in mammalian cells in vitro, wherein the tetR gene is devoid of any splice signals and is modified to optimize codon usage for mammalian cells and to increase the percentage of G and C bases while maintaining a low frequency of CpG base pairs, said method comprising introducing said tetR gene to said mammalian cells, and culturing said mammalian cells under conditions sufficient for the expression of said tetR gene.

6. A transgenic mouse having a transgene integrated into its genome, wherein the transgene comprises an optimized tetR gene having a sequence set forth in FIG. 16 (SEQ ID NO: 20) in operable linkage with an unmodified PEPCK promoter, and wherein said transgene is expressed in the cells of said mouse at a level sufficient to produce the optimized tetR protein.

7. A transgenic mouse according to claim 6 further having a second transgene integrated into its genome, wherein said second transgene comprises a gene of interest in operable linkage with a PEPCK promoter element modified to contain a tetR operator at the NheI site, wherein in the absence of a tetracycline compound, expression of said gene of interest is repressed in the cells of said mouse, and in the presence of a tetracycline compound in the mouse, said gene of interest is expressed in the cells of the mouse causing said mouse to exhibit a detectable and functional phenotype as compared to a wild-type mouse.

8. A method of selectively inducing the expression of a gene of interest in a transgenic mouse comprising administering a tetracycline compound to the transgenic mouse of claim 7, wherein said tetracycline compound induces the expression of said gene of interest.

9. A transgenic mouse having a transgene integrated into its genome, wherein the transgene comprises the optimized tetR gene of claim 2 in operable linkage with an unmodified PEPCK promoter, wherein said transgene is expressed in the cells of said mouse at a level sufficient to produce the optimized tetR protein in an amount effective to regulate expression of a gene of interest upon its introduction into said mouse at an embryonic stage, and wherein said gene of interest is in operable linkage with a PEPCK promoter element modified to contain a tetR operator at the NheI site.

10. A transgenic mouse according to claim 9 further having a second transgene integrated into its genome, wherein said second transgene comprises a gene of interest in operable linkage with a PEPCK promoter element modified to contain a tetR operator at the NheI site, wherein in the absence of a tetracycline compound, expression of said gene of interest is repressed in the cells of said mouse, and in the presence of a tetracycline compound, said gene of interest is expressed in the cells of the mouse causing said mouse to exhibit a detectable and functional phenotype as compared to a wild-type mouse.

11. The transgenic mouse of claim 10, wherein said gene of interest is the gene encoding bovine growth hormone, and wherein in the absence of a tetracycline compound, the expression of bovine growth hormone is repressed, and in the presence of a tetracycline compound, said gene encoding bovine growth hormone is expressed in the cells of the mouse causing said mouse to exhibit accelerated growth as compared to a wild-type mouse.

12. A method of selectively regulating the expression of a gene of interest in a transgenic mouse comprising administering tetracycline, or functionally related compound, to the transgenic mouse of claim 11, wherein said tetracycline, or functionally related compound, regulates the expression of said gene of interest.

* * * * *